United States Patent [19]

Lorenzen et al.

[11] Patent Number: 5,730,123
[45] Date of Patent: Mar. 24, 1998

[54] MEDICAL MULTIPLE ACCESS LOW DEAD SPACE ANTI-MICROBIAL ASPIRATING/ VENTILATING CLOSED SYSTEM IMPROVEMENTS AND METHODS

[75] Inventors: Rick D. Lorenzen, Ogden; Darrel R. Palmer, Sandy; William R. Houghton, Midvale; Gerry A. Arambula; David Theron Van Hooser, both of Salt Lake City; Richard C. Lambert, Highland; Billy M. Jensen, Sandy; Gene Stewart, Midvale, all of Utah

[73] Assignee: Ballard Medical Products, Draper, Utah

[21] Appl. No.: 426,362

[22] Filed: Apr. 21, 1995

Related U.S. Application Data

[62] Division of Ser. No. 245,333, May 18, 1994, abandoned.

[51] Int. Cl.⁶ .................... A61M 16/00; A61M 11/00; A61M 5/00; A62B 9/06
[52] U.S. Cl. ............ 128/207.14; 128/912; 128/DIG. 26; 128/207.16; 128/203.12; 128/200.26; 128/202.27; 604/93; 604/171; 604/187
[58] Field of Search .......... 128/200.26, 207.14–207.16, 128/DIG. 26, 911, 912; 604/93, 171, 187, 264

[56] References Cited

U.S. PATENT DOCUMENTS

| | | | |
|---|---|---|---|
| 3,633,586 | 1/1972 | Sheridan | 128/207.14 |
| 3,794,026 | 2/1974 | Jacobs | 128/145.8 |
| 4,214,593 | 7/1980 | Imbruce et al. | 128/748 |
| 4,327,718 | 5/1982 | Cronenberg | 128/205.12 |
| 4,333,451 | 6/1982 | Paluch | 128/205.12 |
| 4,502,482 | 3/1985 | DeLuccia et al. | 128/207.15 |
| 4,512,765 | 4/1985 | Muto | 604/119 |
| 4,607,635 | 8/1986 | Heyden | 128/207.15 |
| 4,632,112 | 12/1986 | Matthews | 128/207.14 |
| 4,634,433 | 1/1987 | Osborne | 604/171 |
| 4,637,389 | 1/1987 | Heyden | 128/207.15 |
| 4,661,110 | 4/1987 | Fortler et al. | 604/256 |
| 4,669,463 | 6/1987 | McConnell | 128/207.14 |
| 4,821,714 | 4/1989 | Smelser | 128/207.14 |
| 5,029,580 | 7/1991 | Radford et al. | 128/207.14 |
| 5,083,561 | 1/1992 | Russo | 128/207.16 |
| 5,346,478 | 9/1994 | Jinotti | 604/171 |
| 5,490,503 | 2/1996 | Hollister | 128/205.12 |
| 5,507,279 | 4/1996 | Fortune et al. | 128/207.14 |

*Primary Examiner*—Kimberly L. Asher
*Attorney, Agent, or Firm*—Workman Nydegger & Seeley

[57] ABSTRACT

Apparatus and methods are disclosed by which a closed ventilating system accommodates multiple access to the respiratory system of an intubated medical patient without comprising the closed character of the system. Access to the respiratory system through one or more access sites of the closed system apparatus is provided at proximal adapter ports to ventilate the lungs of the patient with gas or gases, to aspirate secretions from the lungs, to oxygenate the lungs to eliminate or reduce residual $CO_2$ therefrom, to visually inspect selected parts of the respiratory system, to sample sputum and gases, to sense parameters such as flow rates, pressure, and temperature, to flush with washing solution, and/or to administer medication, gases, and/or lavage.

27 Claims, 12 Drawing Sheets

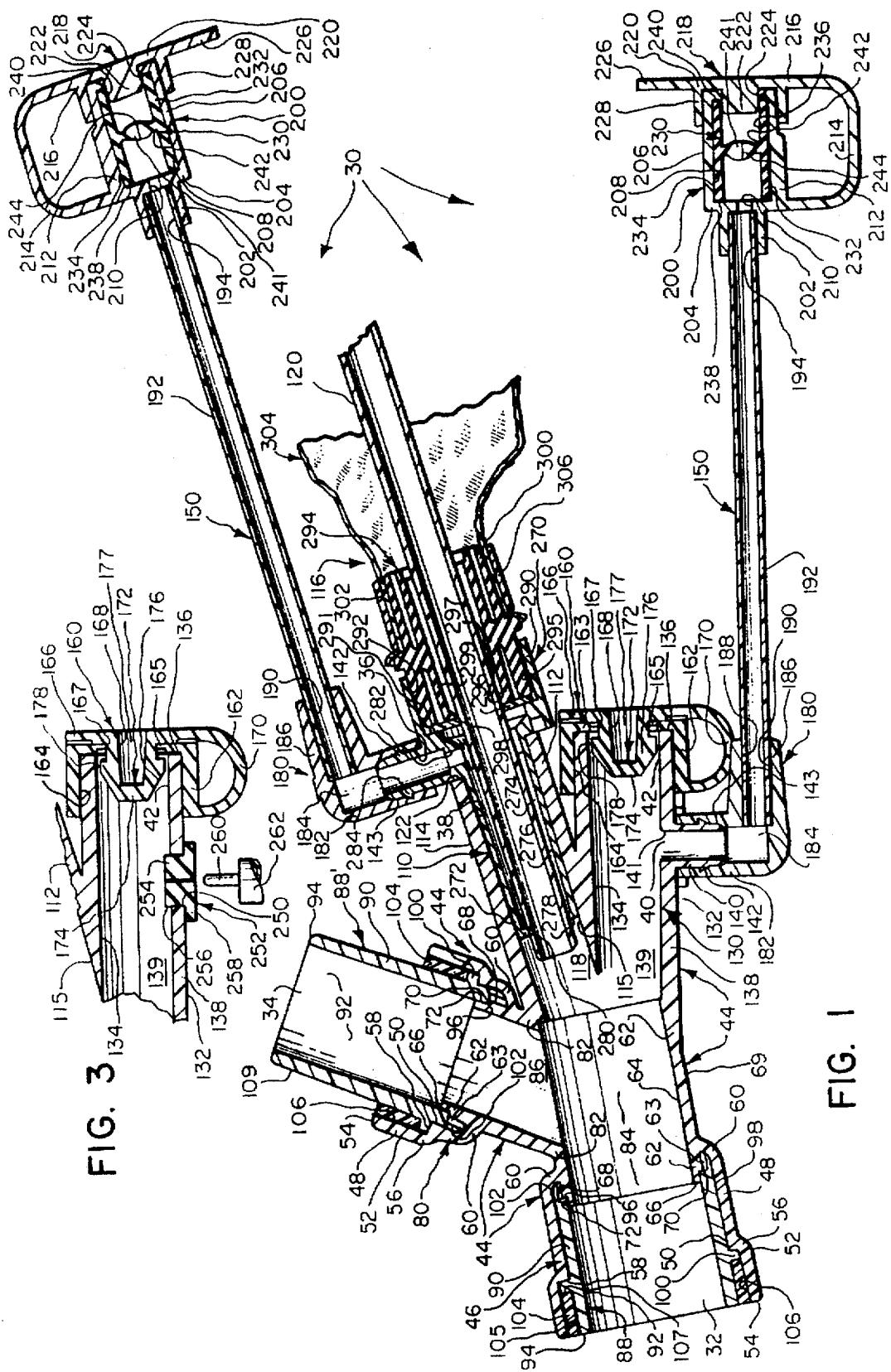

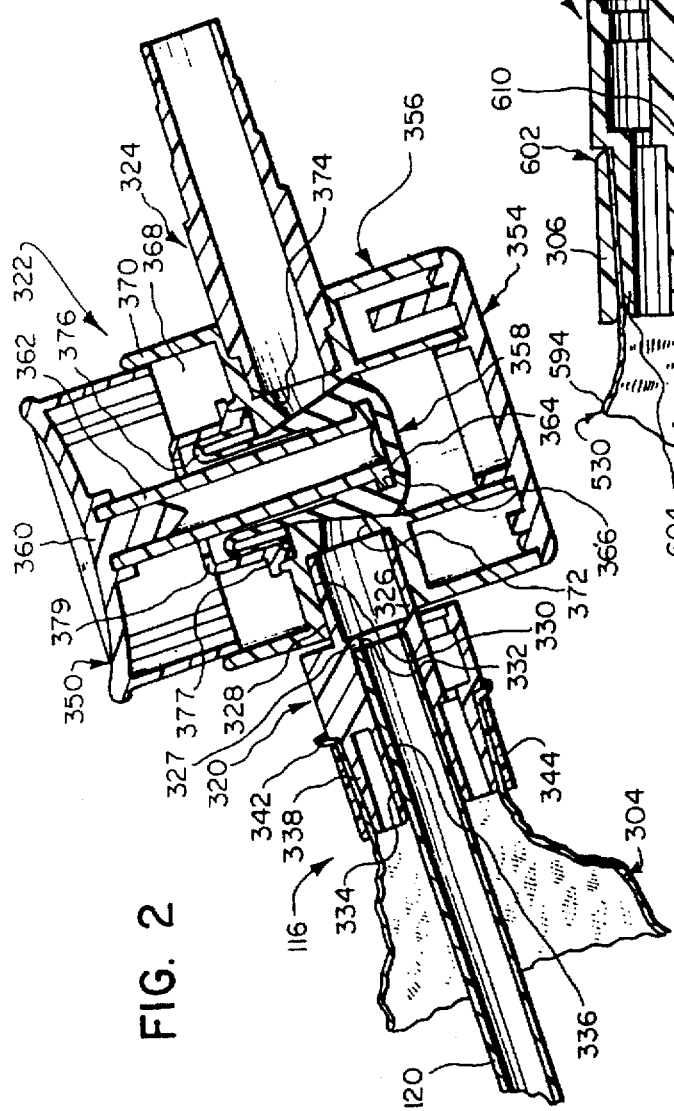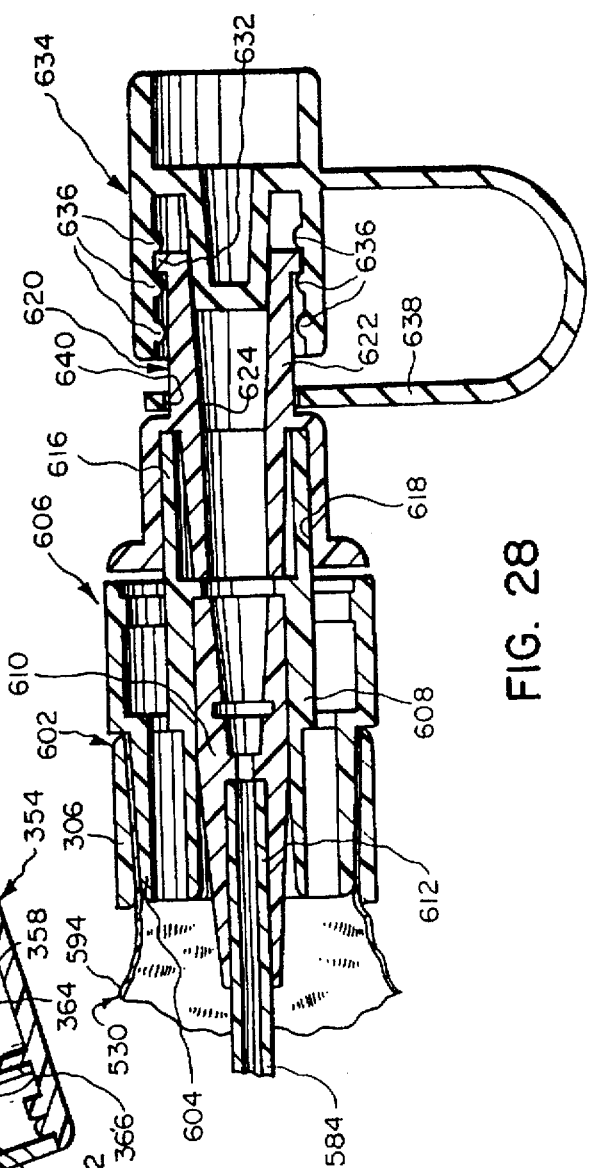

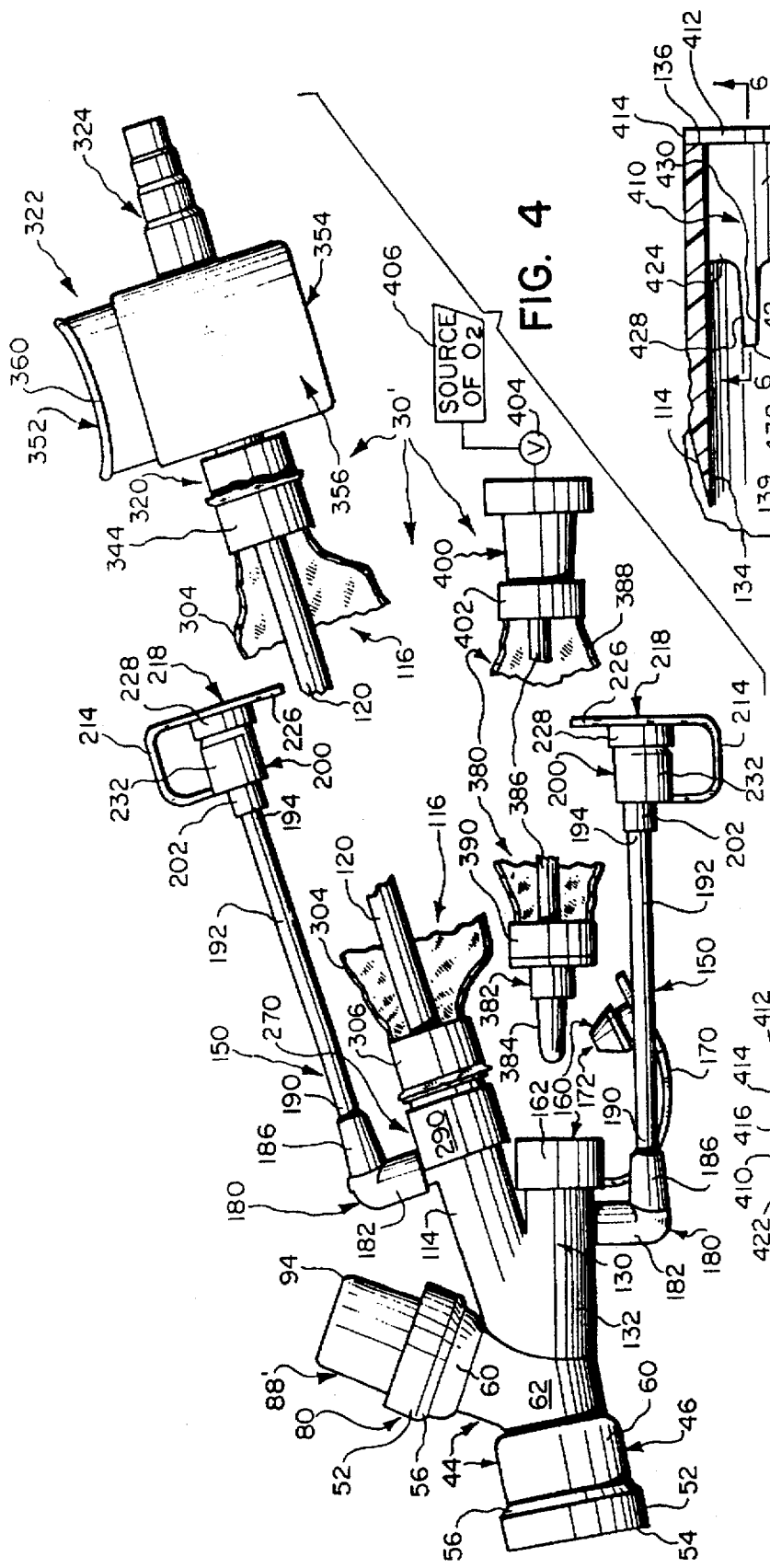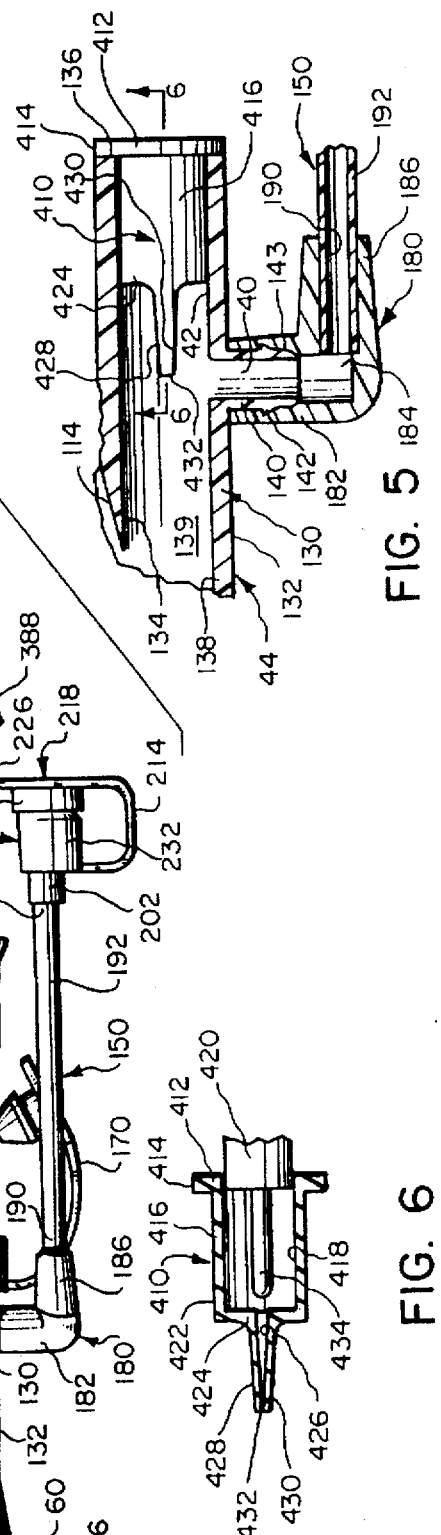

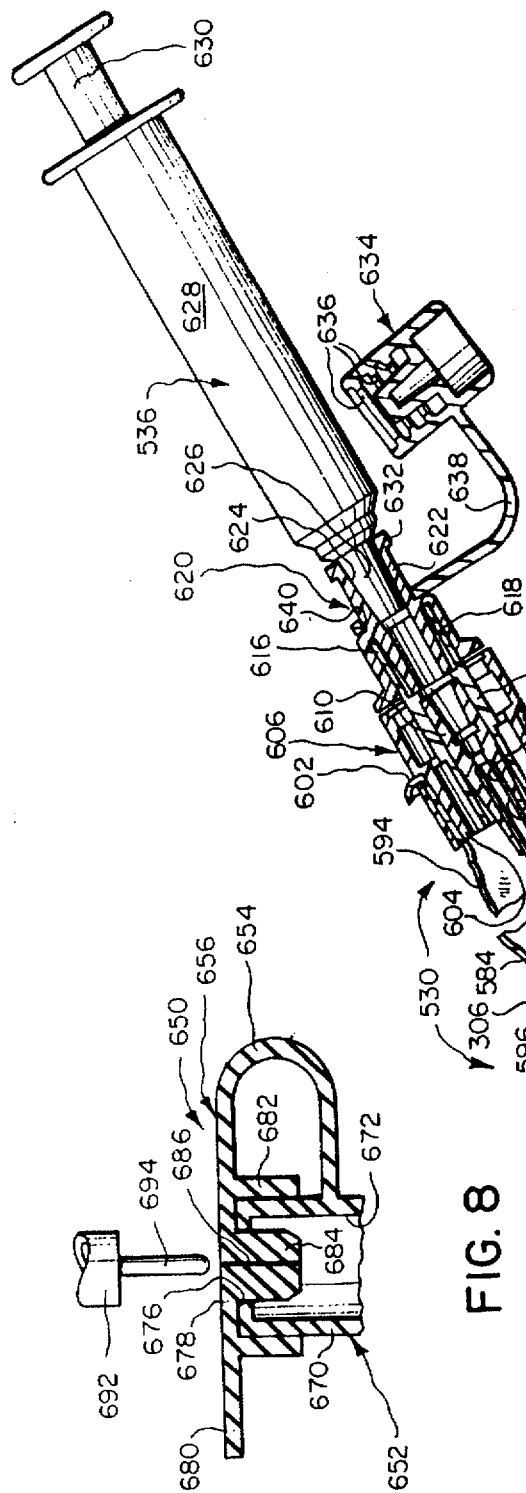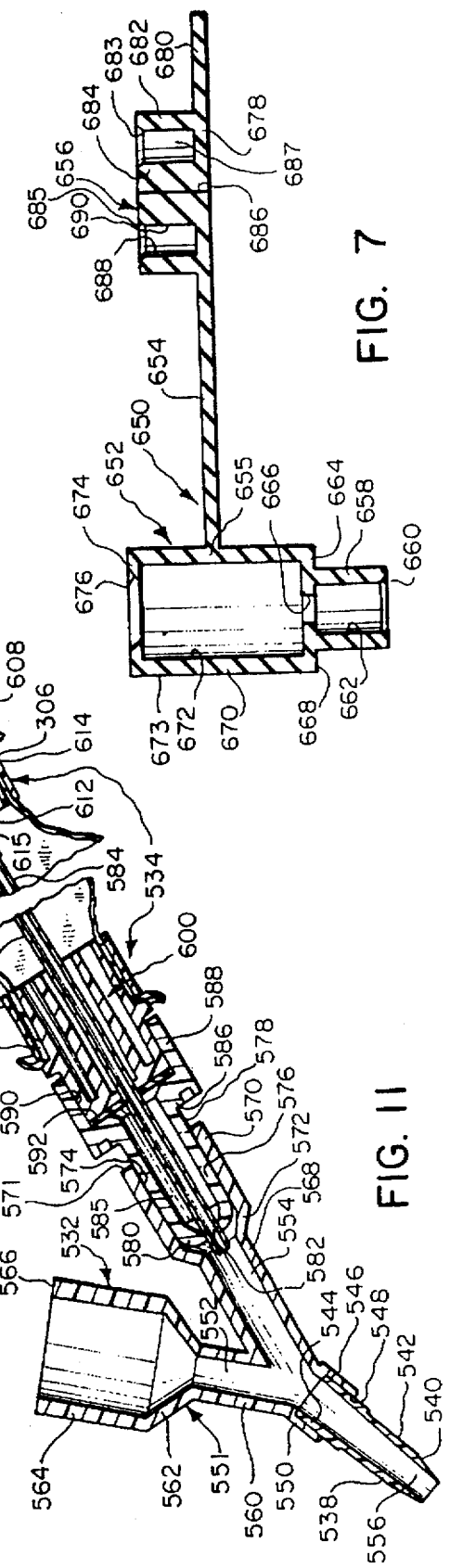

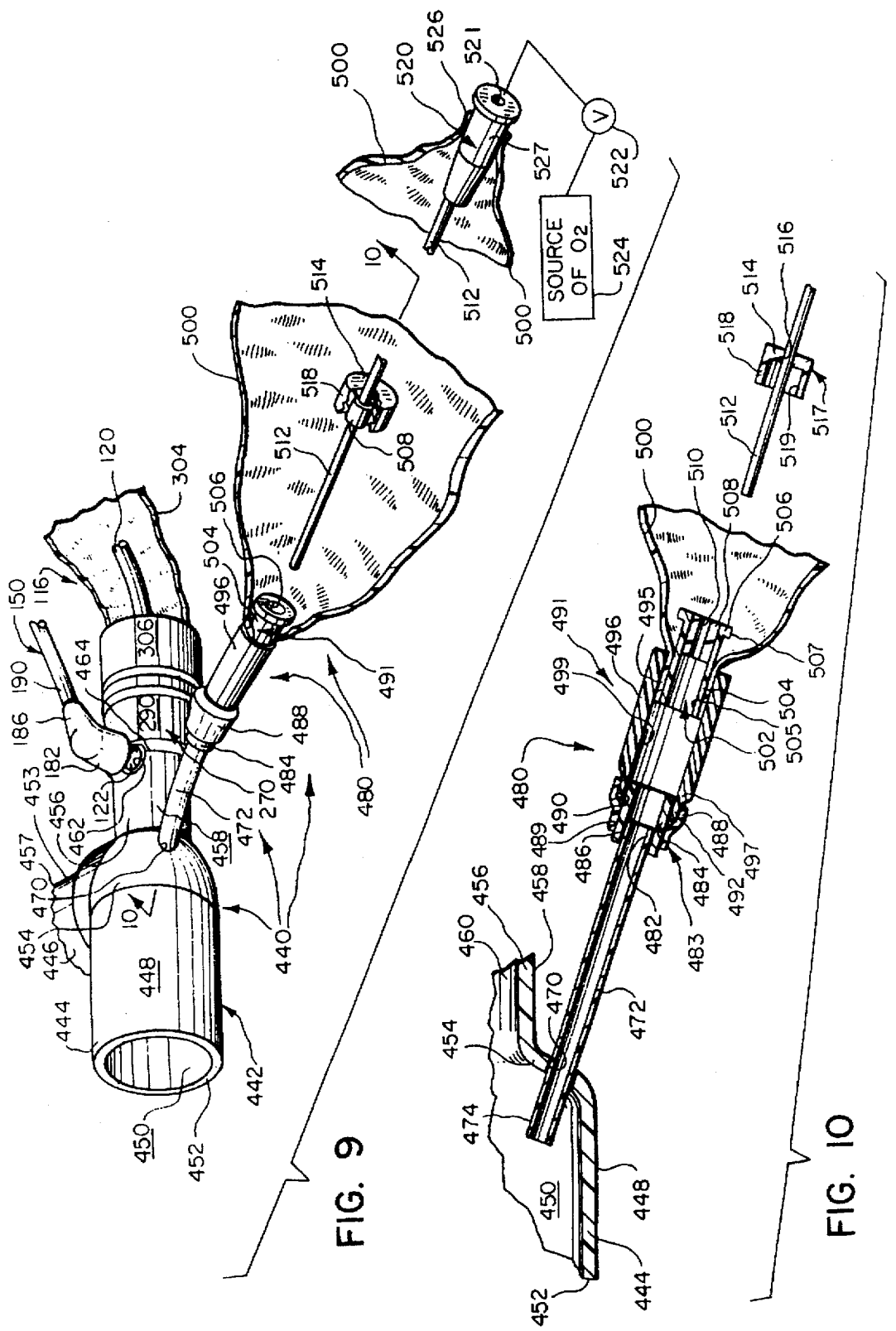

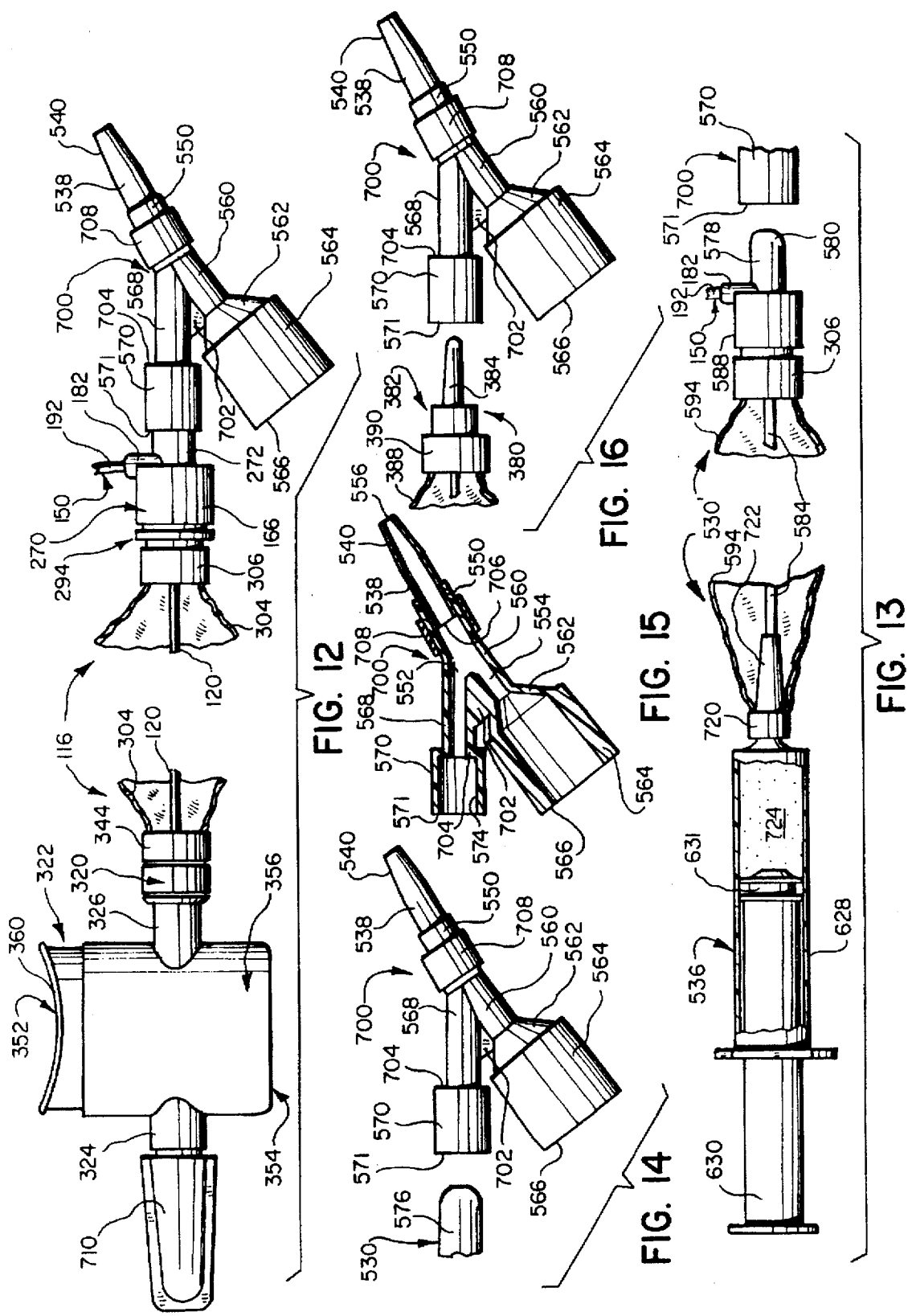

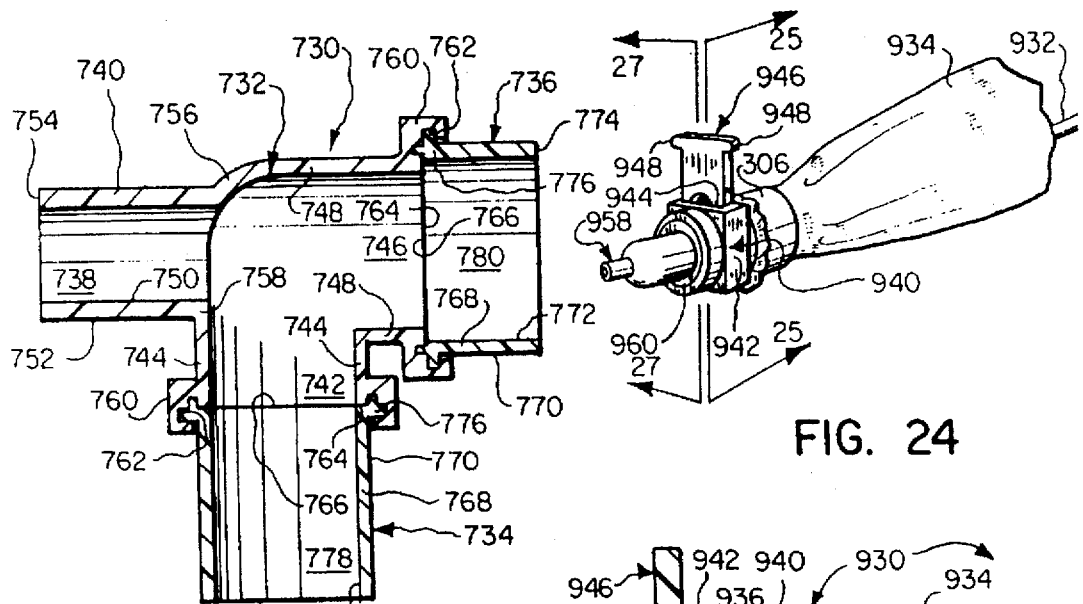
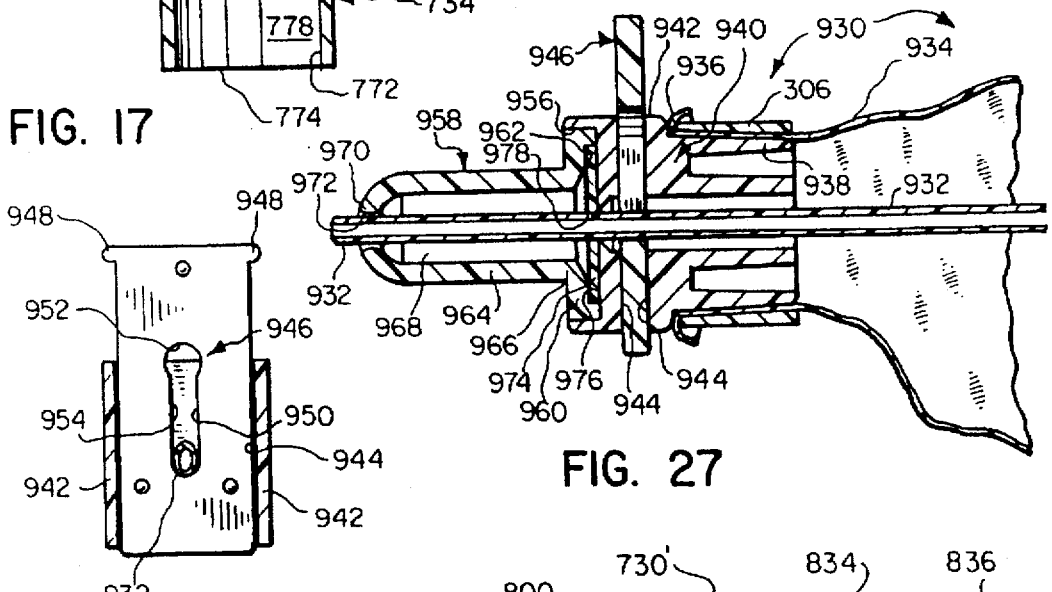
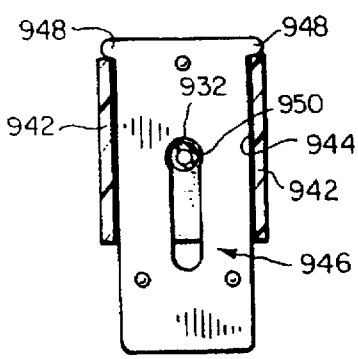
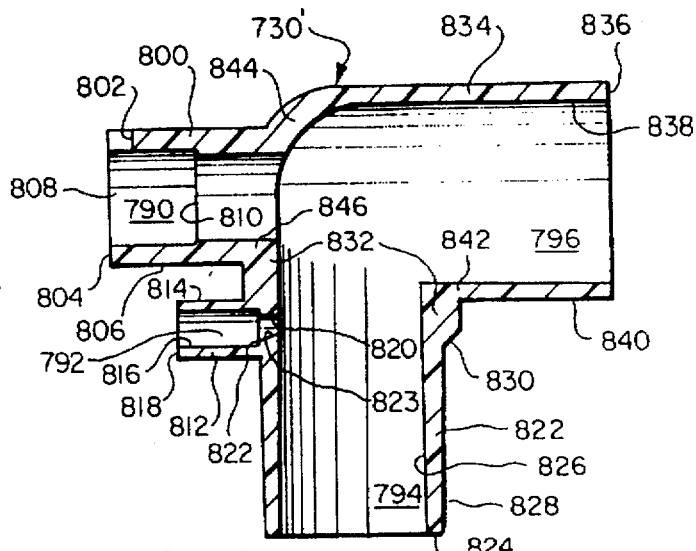

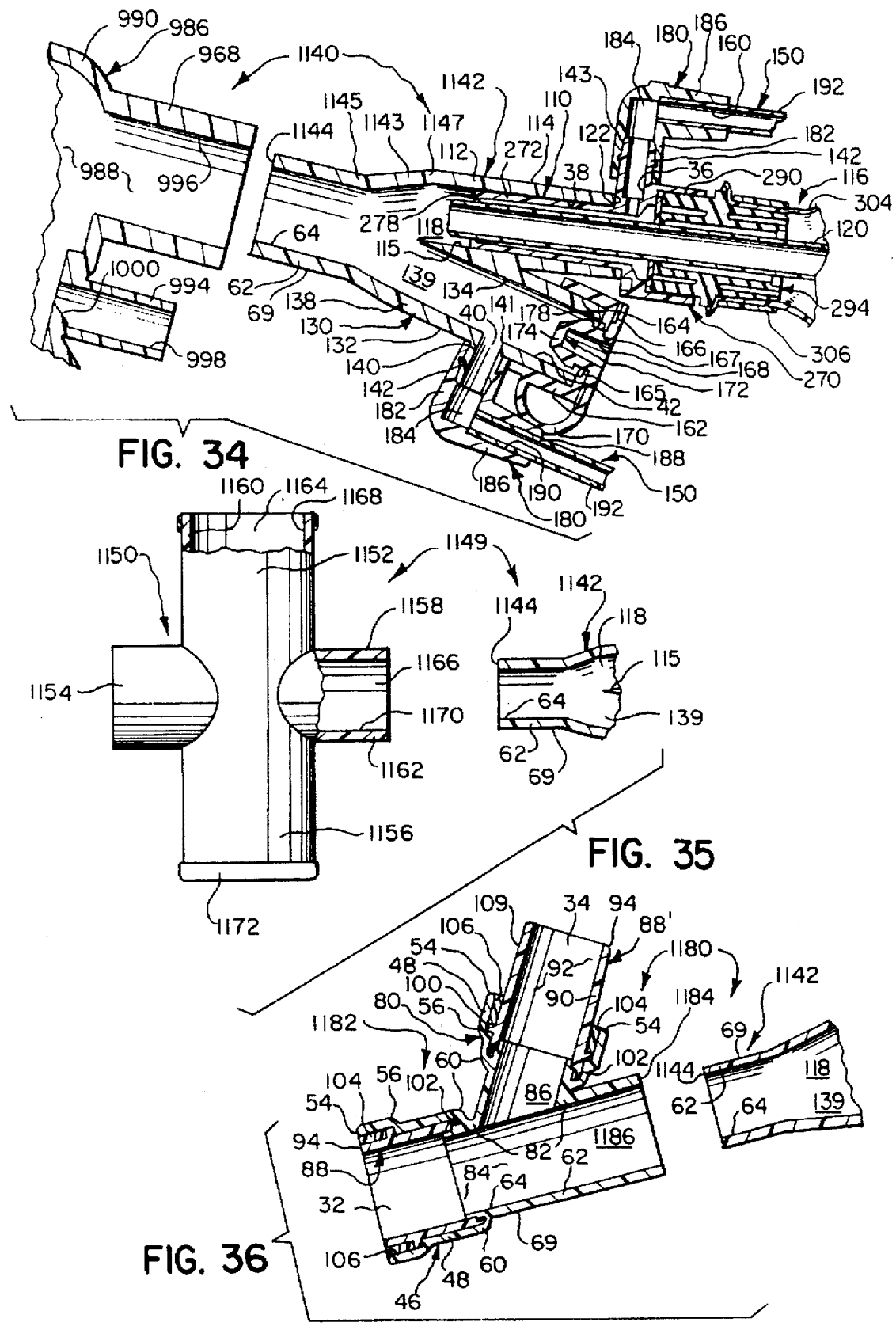

1

MEDICAL MULTIPLE ACCESS LOW DEAD SPACE ANTI-MICROBIAL ASPIRATING/ VENTILATING CLOSED SYSTEM IMPROVEMENTS AND METHODS

This application is a division of our U.S. patent application Ser. No. 08/245,333 filed May 18, 1994, now abandoned.

FIELD OF INVENTION

The inventions disclosed herein relate generally to improved medical care for intubated patients, and more particularly to novel multiple access, low dead space improvements, and related methods, for ventilating, aspirating, monitoring, sampling, and providing therapeutic delivery to the respiratory tract of intubated medical patients, including infants, adolescents, and adults.

BACKGROUND

Respiratory patient care is a dynamically developing field in medicine, ranging in its needs from infants to the aged. The range of respiratory ailments, both temporary and permanent, to which such patients are subjected are many and varied. The frontier of medical knowledge is advancing and recommended treatments have become a blend of old and more recent discoveries.

Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern. Other equipment problems also exist which concern preventing cost-oriented, unsafe extended use of ventilating, aspirating, and other respiratory access apparatus, reliability during use, quick and reliable removal and exchange of spent aspirating and ventilating devices without comprising the quality of health care provided to the patient, avoiding intentional or inadvertent conversion from a closed system to an open system, prevention of stress and/or occlusion of flow passageways to and from the patient's respiratory system, avoidance of a large inventory of a variety of incompatible products providing easy, fail-safe access for multiple purposes.

By way of an example only, with low lung capacity patients, such as premature babies and adults suffering from emphysema, is the removal of accumulated lung secretions without starving the patient for oxygen (thereby causing undesirable side effects) during the secretion removal process.

Sight must not be lost as to the deficiencies in prior proposals in terms of risks created for the health care provider. Largely, proposals of the past have ignored the needs of the health care provider to attain a reasonable measure of protection from contamination by the patient.

Providing apparatus and methodology having the capacity to promptly, efficiently, safely, and cost effectively address the health care needs of intubated patients across the entire spectrum of respiratory ailments comprises, prior to the present invention, a largely unresolved need. The range of procedures comprise: ventilating, aspiration, oxygenation, sampling, visual inspection, in-line sensing, pressure monitoring, flushing, and medication and/or lavage. Better protection for the health care provider has been a long-term unsatisfied need.

BRIEF SUMMARY AND OBJECTS OF THE PRESENT INVENTION

In brief summary, the present invention substantially alleviates the aforesaid problems of the prior art and comprises apparatus and methods by which a closed ventilating system accommodates multiple access to the respiratory system of an intubated medical patient without compromising the closed character of the system. Access to the respiratory system through one or more access sites of the closed system apparatus is provided to ventilate the lungs of the patient with gas or gases, to aspirate secretions from the lungs, to oxygenate the lungs to eliminate or reduce residual $CO_2$ therefrom, to visually inspect selected parts of the respiratory system, to sample sputum and gases, to sense parameters such as flow rates, pressure, and temperature, to flush with washing solution, and/or to administer medication, gases, and/or lavage.

The preferred system is unitized into severable and disposable components which are cost effective and accommodate good health care practices while promoting limitations on duration of use well within appropriate medical tolerances. Quick removal and replacement of discarded components is accommodated without introduction of additional risks to the patient. The technology of the present invention has substantial universal application to all respiratory patients, ranging from infants to the aged.

With the foregoing in mind, it is a primary object of the present invention to substantially alleviate problems of the prior art in the field of respiratory care for medical patients.

It is an additional dominant object of the present invention to provide apparatus and related methods by which a closed ventilating system is able to accommodate multiple access to the respiratory system of an intubated medical patient.

An additional paramount object is the provision of novel apparatus and related methods by which a closed ventilating system accommodates multiple access to the respiratory system of an intubated medical patient without compromising the closed character of the system.

An additional object of the present invention is the provision of access through one or more access sites in a closed system respiratory apparatus to accommodate ventilating of the lungs of the patient with gas or gases, to aspirate secretions from the lungs, to oxygenate the lungs to eliminate or reduce residual carbon dioxide therefrom, to visually inspect selected parts of the respiratory system, to sample sputum and gases, to sense parameters such as flow rates, pressure, and temperature, to flush with washing solution and/or to administer medication, gases, and/or lavage, and related methods.

An additional significant object is the provision of a closed respiratory health care system unitized into severable and disposable components which are cost effective and accommodate good health care practices while promoting limitations on duration of use well within appropriate medical tolerances.

It is an additional valuable object to provide for quick removal and replacement of discardable components toward the end of their useful life in a respiratory health care system and to accommodate such without introduction of additional risks to the patient.

It is another dominant object to provide a respiratory health care system and related methods which has substantial universal application to all respiratory patients ranging from infants to the aged.

It is a further object of significance to provide a respiratory health care system and related methods by which superior protection is provided by the care giver to an intubated patient.

It is a further object of the present invention to provide novel respiratory systems and related methods comprising a plurality of entry sites normally sealed to minimize introduction of contamination and avoid loss of ventilating gas, but yet to allow entry of an instrument, device, or the like.

It is a primary object of the present invention to provide a unitized respiratory health care system and related method where components of the system comprise disposable segments which may be facilely connected and removed by the care giver.

A further important object of the present invention is to provide features in a respiratory health care system which avoid imposition of stress on the components and prohibit occlusion of flow pathways.

A further object of the present invention is the provision of a novel respiratory health care system wherein an oxygenation, aspiration, and/or sampling catheter tube can be locked into a selected inserted position.

It is a prominent object of the present invention to provide respiratory health care systems and related methods which accommodate simultaneous access to and treatment within the respiratory system of a medical patient.

It is a further object of the present invention to provide novel respiratory health care systems and related methods having minimal dead space.

These and other objects and features of the present invention will be apparent from the detailed description taken with reference to the accompanying drawings.

BRIEF DESCRIPTION OF THE DRAWINGS

FIG. 1 is a longitudinal cross-section of one multi-access embodiment of the present invention;

FIG. 2 is a longitudinal cross-section of the proximal end of the multi-access apparatus illustrated in FIG. 1;

FIG. 3 is a fragmentary cross-section of a modified form of the present invention illustrating two access ports;

FIG. 4 is a fragmentary side elevation of another multi-access embodiment of the present invention;

FIG. 5 is an enlarged fragmentary cross-section of one inlet portion of the apparatus illustrated in FIG. 4;

FIG. 6 is a cross-sectional view taken along lines 6—6 of FIG. 5;

FIG. 7 is an enlarged cross-sectional view of a lavage access port equipped with a slit valve cap to accommodate introduction of medication into the respiratory system of an intubated medical patient;

FIG. 8 is an enlarged fragmentary cross-section of the slit valve cap of FIG. 8, with the cap shown in its inserted position preparatory to receiving a medication probe;

FIG. 9 is a perspective representation of the further multi-access embodiment of the present invention with parts broken away and other parts removed for clarity;

FIG. 10 is an enlarged fragmentary cross-section taken along lines 10—10 of FIG. 9;

FIG. 11 is a longitudinal cross-sectional view of still another multi-access apparatus embodying the principles of the present invention by which medication may be added to the respiratory system of a patient without interruption of the flow of ventilating gases to and from the respiratory system;

FIG. 12 is a fragmentary side elevational view, shown partly in cross-section for clarity, of still another multi-access apparatus embodying the principles of the present invention;

FIG. 13 is an elevational view of still an additional apparatus embodying principles of the present invention, with parts broken away and otherwise shown in cross-section for clarity;

FIG. 14 is a side elevation of the distal adapter forming part of the apparatus of FIG. 12;

FIG. 15 is a longitudinal cross-section of the distal adapter of FIG. 14;

FIG. 16 is an elevational view of the distal firing illustrated in FIGS. 12, 14, and 15 further illustrating a cartridge or component about to be compression fit into the smaller of the two entry ports of the adapter;

FIG. 17 is an enlarged cross-section of a further distal fitting embodying principles of the present invention;

FIG. 18 is an enlarged cross-section of still another distal fitting;

FIG. 24 is a fragmentary perspective illustrating primarily a lock mechanism by which an aspirating or like respiratory catheter tube may be secured in a desired inserted position against inadvertent displacement;

FIG. 25 is an enlarged cross-section taken along lines 25—25 of FIG. 24, illustrating the manner in which the catheter tube is compressed to secure the same in a desired inserted position;

FIG. 26 is an enlarged cross-sectional view similar to FIG. 25, but showing the catheter tube in a released position, which accommodates advancement and retraction of a catheter tube in respect to the locking mechanism;

FIG. 27 is a cross-section taken along lines 27—27 of FIG. 24;

FIG. 28 is a fragmentary enlarged cross-sectional view of a lure lock proximal coupling member embodying the principles of the present invention;

FIG. 34 is an enlarged fragmentary exploded cross-section of an additional multi-adapter embodiment of the invention;

FIG. 35 is an enlarged fragmentary exploded cross-section of still another multi-adapter embodiment of the invention;

FIG. 36 is an enlarged fragmentary exploded cross-section of a further multi-adapter embodiment of the invention;

DETAILED DESCRIPTION OF THE ILLUSTRATED EMBODIMENTS

Figure 19:
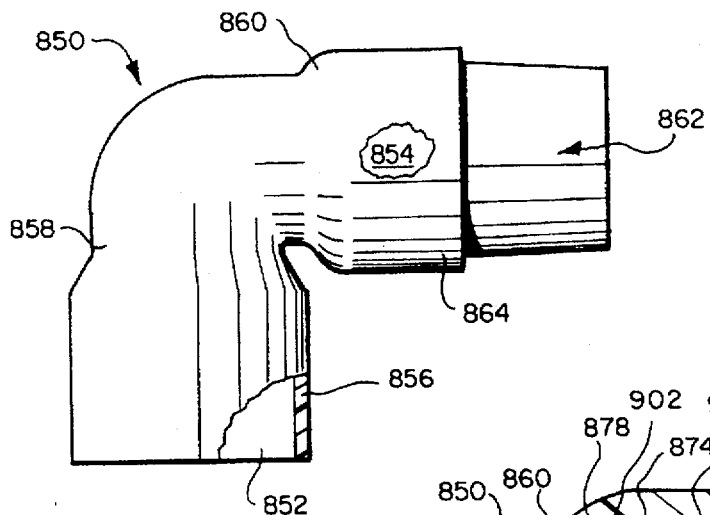
FIG. 19 is an elevational view of an additional distal fitting or adapter, embodying principles of the present invention.

Reference is now made to the drawings wherein like numerals are used to designate like parts throughout. FIGS. 1 and 2 illustrate in longitudinal cross-section a multi-access apparatus, generally designated 30, for use in conjunction with the respiratory tract of an intubated medical patient ranging from infants to the aged. The apparatus 30 comprises a single distal access port 32 and a plurality of proximal access ports 34, 36, 38, 40, and 42. For example only access ports 32 and 34 accommodate continual cyclic patient ventilation, independent of pursuit by the health care provider of any other patient respiratory access procedure. Access port 36 accommodates introduction of irrigation, wash, or lavage liquid by which the exterior of an aspirating catheter tube is washed after the catheter tube is withdrawn following use. Access port 38 accommodates selective insertion and subsequent removal of an aspirating catheter assembly, the catheter tube of which removes secretions from the lungs. Access port 40 accommodates introduction of lavage or medication. Access port 42 accommodates releasible attachment and subsequent removal of an oxygenation catheter assembly, the catheter tube of which is used to replace residual carbon dioxide in the lungs with oxygen, or to accommodate entry of temperature or pressure monitoring instruments or to accommodate obtaining samples of sputum or gases and/or to allow insertion of visual inspection instruments.

The apparatus 30 comprises a tracheal tube adapter, generally designated 44, preferably formed of injection molded rigid medical grade synthetic resinous material, such as acrylic, cyrolite, pebax, polypropylene, or the like. Adapter 44 comprises a hollow female distal bell housing, generally designated 46, which comprises a stepped annular wall 48.

Wall 48 comprises a thickness which is generally uniform, defined by inside and outside surfaces 50 and 52. The distal end of wall 48 is defined by a blunt transverse annular distal edge 54, where the bell housing comprises its largest diameter. Wall 48 comprises a first reduced diameter annular step 56 comprising inside shoulder 58, and a second further reduced diameter annular step 60.

Annular step 60 defines a bifurcation where an annular swivel alignment retaining wall 62 extends distally from the bifurcation with wall 48 adjacent step 60. Walls 48 and 62, where co-extensive, are separated by a blind annular slot 63 which opens distally. Walls 48 and 62 are illustrated as being formed as one-piece. Wall 62 comprises an interior surface 64, illustrated as being of uniform diameter, an exterior surface 69 and a blunt annular transverse distal edge 66. The surface 68 of wall 62 is stepped or notched at shoulder 70. A reduced diameter annular surface 72 of wall 62 extends between edge 66 and shoulder 70 and forms part of a female recess or notch.

Adapter 44 also comprises a second bell housing, generally designated 80, which is constructed to comprise components the same as bell housing 46, although bell housing 80 is somewhat shorter in its axial length. Accordingly, the parts of bell housing 80 have been enumerated the same as bell housing 46 and no further description is needed for one skilled in the art.

Wall 62 of bell housing 46 and wall 62 of bell housing 80 merge at an annular site 82, where a passageway 86 comprising port 34 merges with a passageway 84 comprising port 32.

A sleeve, generally designated 88, is rotatably positioned and secured within the bell housing 46. Sleeve 88 comprises an annular wall 90 comprising an interior surface 92, which is generally annular, but may be slightly divergently tapered from left to right, as viewed in FIG. 1, to accommodate a press-fit but removable union with a proximal fitting of a tracheal tube, for example, in a manner generally well-known to those skilled in the art. Sleeve 88 also comprises a predetermined length between blunt edges 94 and 96. Edge 94 is radially flush with edge 54. Edge 96 rotatably abuts shoulder 70, while the adjacent interior surface 92 rotatably turns contiguously upon surface 72.

Sleeve 88 also comprises a surface 98, which is interrupted by an outwardly directed radially extending retaining flange 100. The location of flange 100 is selected to be adjacent step 56 to accommodate rotation contiguous with shoulder 58. Sleeve 88 also comprises a relatively thin integral deflectably yieldable annular sealing rib or finger 102 directly adjacent blunt shoulder 96. Rib 102 extends proximally in an axial direction.

When sleeve 88 is assembled into the position illustrated in FIG. 1, the sealing rib 102 is caused to forcibly engage a surface within annular slot 63 and be deflected into a firm sealed relation with that surface to thereby hermetically close the interface between sleeve 88 and bell housing 46.

Sleeve 88 is retained in the position illustrated in FIG. 1 by an annular rigid plastic collar 104 positioned between walls 48 and 90 and distally terminated in radially directed edges 54 and 94. Collar 104 is bonded to surface 106 of wall 48. Thus, collar 104 functions as a bushing with flange 100 and surface 105 of sleeve 88 contiguously but rotatably engage the proximal edge 107 and inside annular surface of collar 104.

Sleeve 88', which is rotatably coupled to bell housing 80, is substantially identical to sleeve 88, being rotatably placed within bell housing 80. Sleeve 88' is enumerated identical to sleeve 88, although it will be readily apparent that the sleeve orientation is reversed, the overall length of sleeve 88 is shorter, the sleeve 88' extends beyond bell housing 80 and the radial flange 100 is positioned closer to slot 63.

Ventilating tubing is compression fit into or over the exposed part 109 of sleeve 88'. A tracheal fitting is inserted into the hollow of sleeve 88. Sleeve 88' rotates with any rotation imposed upon the connected ventilating tubing or, alternatively, retain an essentially stationary position if and when the adapter 44 is rotated, either intentionally or inadvertently in respect to sleeves 88 and 88'. Thus, twisting and consequential occluding or partial occluding of ventilating tubing is avoided.

Adapter 44 further comprises an angularly-disposed proximally-directed barrel, generally designated 110. Proximally-directed barrel 110 comprises an annular wall 112, the exterior surface 114 of which is annular, while the interior surface 115 is illustrated as being slightly tapered divergently in a distal direction to receive, in compression-fit relation, an aspirating catheter cartridge, generally designated 116. Cartridge 116 will be explained in greater detail hereinafter.

The interior surface 115 defines a proximal passageway 118, the diametral size of which is substantially smaller than either of the two previously described passageways 84 and 86. Wall 112 merges at annular site 82 with the distal end of bell housing 80 in such a way that passageway 118 merges distally with passageway 84. It should be noted that the longitudinal axis of passageway 84 and the longitudinal access of passageway 118 intersect each other at a relatively small acute angle, which may be on the order of about 20°, to accommodate ease of insertion and centering of a slidable aspirating catheter tube 120, forming part of the aspirating catheter cartridge 116. Catheter tube 120 is flexible along its length to accommodate smooth insertion through a tracheal tube, for example, into either lung of the patient for removal of secretions.

Wall 112 terminates in a blunt transverse proximal edge 122 and is formed as one piece with the other components of adapter 44, excluding swivel sleeves 88 and 88'.

Adapter 44 further comprises a second angularly-disposed proximally directed barrel, generally designated 130. Barrel 130 comprises an exterior substantially cylindrical surface 132, and interior surface 134, which is illustrated as being slightly divergently tapered in a distal direction, for purposes yet to be explained. Barrel 130 terminates in a proximal edge 136, which is blunt and transversely-directed. Barrel 130 comprises a wall 138 of uniform thickness located between surfaces 132 and 134. Wall 138 defines passageway 139, which merges distally with passageway 84, forming a small acute angle therewith of on the order of about 20°, as illustrated in FIG. 1, although other angles could be used. The use of slight acute angles for the proximal passageways or ports functions to facilely center the distal end of a catheter tube as it is inserted through a given proximal passageway. Centering may occur at least in part by acute angle deflection off an interior wall surface of the adapter or the tracheal tube.

Wall 138 is interrupted by a male transversely directed side port tube 140, the hollow interior of which defines access port 40. The tube 140 comprises a smooth interior annular surface 141, illustrated as being of uniform diameter and an exterior surface 143, which is interrupted by an outwardly-projecting radially-directed annular barb 142, by which a medication-administering attachment, generally designated 150, is secured against inadvertent removal. Barrel 130 comprises part of the one-piece construction of adapter 44, as illustrated in FIG. 1.

Barrel 130 is illustrated in FIG. 1 as being closed by a tethered, press-fit cap, generally designated 160. Cap 160 is sized and shaped so as to be snugly received in the position illustrated in FIG. 1, somewhat compressively, so that inadvertent removal does not take place.

Cap 160 is formed, as illustrated, of one piece comprising an annular collar 162, a plug 172, and a tether 170, which connects the collar 162 to the plug 172.

Collar 162 is generally annular in its configuration, comprising wall defined by an inside annular surface 164, the diameter of which is slightly smaller than the diameter of the exterior surface 132 at the proximal end of barrel 130, so that the collar 162 must be force-fit into the position illustrated in FIG. 1 and remains in the illustrated position unless intentionally manually removed.

Tether 170 serves to prevent disassociation of the plug 172 from the collar 162 independent of whether plug 172 is in its closed or open position. Collar 162 merges with a proximal inwardly-projecting radially-directed annular wall 163, which is contiguous with edge 136. Wall 163 comprises a reduced thickness region 165 which surrounds a central opening 167, the diameter of which is substantially less than the interior transverse dimension of barrel 130 at edge 136.

Plug 172 comprises a radially-directed annular wall or flange 166, which centrally merges with a distally-extending truncated cone-shaped tip comprising forward blunt transversely oriented wall 174 and tapered wall 176, with which wall portion 174 merges. An annular wall portion 177 connects flange 166 with tapered portion 176. The hollow nature of the annular portion 177 comprises a blind bore 168.

The zenith or maximum diameter at 178 of the tapered wall portion 176 is less than the inside transverse dimension of the barrel 132 adjacent edge 136 and greater than the diameter at aperture 167. The diameter at aperture 167 is greater than the outside diameter of annular wall 177. Accordingly, the distal head of the plug 172 is closed when forced through aperture 167, causing wall 165 to compressively engage the outside surface of annular wall 177 to hold the plug in its closed position. This requires that the tapered wall portion 176 also be forced through aperture 165 both during insertion and removal.

The sleeve 162 at all times is intended to remain in the position illustrated in FIG. 1. The plug 172 may be manually placed in its closed position of FIG. 1 or in its open position illustrated in FIG. 4.

By closing the access port 42 with the plug 160, introduction of microbes and other undesired contamination is prevented. Yet, the cap 160 can be quickly and easily manually removed to accommodate introduction through access port 42 of medication, an oxygenation catheter tube, monitoring devices, sampling devices, and visual inspection, instruments, etc.

The attachment 150, connected to transverse tube 140, comprises a distal fitting, generally designated 180, which is L-shaped in configuration, as illustrated. A first hollow leg 182 of fitting 180 is force-fit over barb 142 and around the exterior surface 143 of tube 140 as illustrated in FIG. 1. Leg 182 comprises a hollow interior 184 aligned with access port 40 through which liquid may be selectively communicated. Fitting 180 comprises a second hollow leg 186, disposed, as illustrated, at approximately 90° in respect to leg 182. Leg 186 comprises a hollow interior bore 188, disposed at approximately right angles to passageway 184 into which a distal end 190 of a flow accommodating tube 192 is placed, either in a compression fit relation, or so as to be bonded or plastic welded in position. Tube 192 may be of any desired length.

Attachment 150 comprises, in addition, a proximal fitting, generally designated 200. Proximal fitting 200 comprises a distal boss 202, into which proximal end 194 of tube 192 is either force-fit or secured as by plastic welding, bonding, or the like. Boss 202 merges, at shoulder 204, into an enlarged annular wall 206. Communication between the hollow interior at the proximal end 194 of tube 192 and the hollow interior 208 within wall 206 is accommodated at orifice 210, the diameter of which is illustrated as being smaller than the inside diameter of tube 192. Wall 206 is thicker at region 212, to accommodate connection of a tether 214 so as to avoid risk that the tether 214 will become severed from the wall 206, with which it is formed initially as one piece. Tether 214 connects at site 216 to a press-fit cap, generally designated 218. Cap 218 comprises a proximal wall or flange 220, centrally thicker at 222 to accommodate being press-fit into proximal opening 224 in the fitting 200. The proximal wall 220 comprises an extension 226, which the user may manually grasp to remove the cap 218 from its closed position, which is illustrated in FIG. 1. Cap 218 also comprises an external annular collar 228, the interior diameter of which is slightly less than the exterior diameter of wall 206, accommodating a press-fit union, which can be manually removed when desired, but will not inadvertently separate.

Wall 206 defines a hollow interior cylindrical chamber surrounded by annular surface 208 in which a cylindrically shaped slit valve, generally designated 230, is disposed. In cross-section, slit valve 230 is generally "T"-shaped, as seen in FIG. 1, and comprises an end-to-end length substantially equal to the interior length of cylindrical wall 208. Slit valve 230 may be formed of silicone rubber, Kraton, or the like, and comprises an annular wall 232 of uniform thickness throughout, as illustrated, comprising an external surface 234, an internal surface 236, as well as blunt transversely disposed distal and proximal edges 238 and 240.

A contoured radially-directed double dome-shaped central wall or diaphragm 241 expands across and normally closes the space within interior surface 236. Web or wall or diaphragm 230 is necked down at the annular site 242 where diaphragm 240 joins wall 232, as one piece, making annular site 242 the weakest part of wall 240, exclusive of one or more central slits 244. Slit 244 may be of any desired size so as to be capable of receiving a hollow male end of an instrument therethrough, which may be utilized to serve any number of purposes. For example, respiratory medication may be applied through a hollow male projection physically inserted through slit 244, through which the medication may be dispensed under aerosol pressure or by manually-generally pressure, for example. The slit 244 is illustrated as being located both at the center of the slit valve 230 and in the region of greatest thickness of wall 241. By providing a centrally thicker wall accompanied by a peripherally weakened wall, at 242, the periphery yields more readily allowing somewhat of coordinated rotation in the wall at both the periphery 242 and at slit 244 when a male projection is physically forced through and removed from the slit 244 both when there is pressure and when there is no pressure at the interior site of the diaphragm 241. Also, the double domed configuration of the diaphragm 241 with the enlarged lips at the slit 244 enhances a return to the normally closed state upon removal of the male projection.

In lieu of the male side wall tube 140 and attachment 150, a slit valve may be placed directly in the wall 138, as illustrated in FIG. 3. More specifically, wall 138 in FIG. 3 is equipped with an aperture 250, of pre-determined size. A slit valve plug, generally designated 252, sized appropriately, and formed of yieldable synthetic resinous material, is force-fit at cylinder 254 thereof so that the memory of the material from which slit valve 252 is formed compressively holds the annular surface 256 forcibly against aperture surface 250. Slit valve 252 is illustrated as comprising an enlarged annular flange 258 disposed external of the outside surface 132 of wall 138, to prevent displacement of the entire slit valve 252 into the hollow passageway 139 when forcibly engaged by hollow male projection 260 of a medication or saline dispenser or container 262.

Returning to FIGS. 1 and 2, the previously mentioned aspirating catheter cartridge or assembly 116 comprises the mentioned aspirating catheter tube 120, illustrated as being of uniform thickness and inside and outside diameter throughout, and a distal fitting, generally designated 270. Fitting 270 comprises a slightly tapered distally-directed wall 272, shown as being in spaced relation to and telescopic surrounding catheter tube 120, catheter tube 120 being illustrated in FIG. 1 in a withdrawn state. A space or chamber 274 exists between the exterior surface of the catheter tube 120 and the interior surface 276 of wall 272. Wall 272 distally merges with an inwardly-directed transverse or radial flange 278 formed as one piece with wall 272. Inwardly-directed annular flange 278 defines a central circular opening at surface 280 through which tube 120 contiguously though slidably extends.

Wall 272 is interrupted by transverse opening 282, which is aligned with the hollow interior of a transverse, relatively short hollow male projection 284. Projection 284 is formed as one piece with wall 272. Excluding length, hollow male projection 284 is constructed substantially identical to the construction of hollow male projection 140 and is correspondingly enumerated. No further description is necessary to impart an understanding to one of skill in the art. The hollow male projection 284 is connected to a second attachment 150, which is constructed identical to previously described attachment 150 and is so enumerated in FIG. 1. The attachment 150 of the aspirating catheter cartridge 116 may be used to wash the exterior and interior surfaces of the catheter tube after it is withdrawn from the patient, saline or other suitable wash solution being introduced by a hollow male projection extended through slit 244 and thence along the hollow interior of attachment 150 of catheter cartridge 116 through opening 282 into chamber 274. The inwardly-directed flange 278 limits passing of the wash solution into the chamber 118 and from thence into the respiratory tract of the patient. Used wash solution is evacuated through the hollow of the catheter tube 120 due to suction applied there. Also, lavage may be introduced through attachment 150, in the manner explained above, when the catheter tube 120 is fully or partially inserted, which lavage runs slowly down the catheter tube into the respiratory tract.

The distal fitting 270 comprises an exposed trailing or proximal annular flange 290, which, prior to assembly comprises a collar having a hollow interior defined circumferentially by interior surface 292. A sheath-holding, tube wiper compression applying double wall collar, generally designated 294 is force-fit at its distal outside wall within the hollow interior of the collar 290, after an annular washer 296 is placed within the hollow of the wall 290 so as to abut shoulder 291. The disk or washer 296 is preferably formed of yieldable synthetic resinous material, such as silicone rubber, and has an inside diameter at aperture-defining surface 298 so as to compressively engage the exterior surface of the catheter tube 120. Thus, the catheter tube 120 is wiped by surface 298 as it is withdrawn from use in the respiratory system of an intubated medical patient, thereby removing secretions and other materials carried upon the exterior surface of the catheter tube 120 and depositing the same in the wash chamber 274.

The double flange fitting 294 provides a certain amount of radially compressibility, which accommodates ready compression fit insertion within wall 290 with the forward edges of inside collar wall 295 and the outside collar wall 299 holding washer 296 in the illustrated position of FIG. 1 and aperture-defining surface 297 providing guidance to the catheter tube as it is displaced.

In addition, the distal end 302 of a collapsible, preferably transparent, plastic sheath, generally designated 304 is placed over the trailing outside annular collar surface 300 of 295. Sheath end 302 is held in compression-fit relationship by a collar 306 forced over the concentrically disposed end 302 and flange surface 300.

Reference is now made to FIG. 2, which illustrates the proximal end of the aspirating catheter cartridge 116. The proximal end of the cartridge 116 comprises seriatim a proximal fitting 320 disposed at the end of the collapsible sleeve or envelope 304, a normally closed suction valve, generally designated 322 and an exteriorally stepped tube, generally designated 324. Fitting 320 is illustrated as being formed as one piece from suitable synthetic resinous material and comprises a trailing or proximal collar 326, the exterior annular surface 328 of which is substantially the same diameter as the diameter of bore 330 forming a part of valve 322. The collar 326 is secured in the position illustrated in FIG. 2 by plastic welding, bonding, or any other suitable fashion.

The hollow interior of collar 326, at radially-directed wall 327 thereof, defines an aperture 332. Fitting 320 also comprises an annular distally-extending interior flange 334, which defines a hollow interior shown as having a uniform diameter extending to aperture 332, into which the trailing end 336 of catheter tube 120 is inserted and secured suitably in the installed position by an appropriate bonding agent, plastic welding, or in any other suitable fashion.

Fitting 320 comprises an exterior, distally-directed flange 338, which is radially spaced from flange 334. The trailing end 342 of the collapsible sheath 304 is contiguously placed over the exterior surface of flange 338, over which a collar 344 is force-fit to retain the end 342 in the assembled position.

When the normally closed valve 322 is manually depressed, negative pressure or suction is delivered from a suitable suction source along a suction tube to the hollow interior of fitting 324 passes across valve 322, through hollow passageways therein, through aperture 332, and along the hollow interior of tube 120 when the distal end of the tube 120 is suitably positioned within a selected lung of the patient. As a consequence, secretions accumulated in the lung are suctioned along the hollow interior of the tube 120 across aperture 332, the hollow interior of the control valve 322 and thence through stepped tube 324.

The control valve 322 comprises a manually actuated reciprocable plunger, generally designated 350, a base plate 354, a female housing member generally designated 356, and a single element elastomeric member, generally designated 358.

Plunger 350 comprises an oval-shaped exposed actuator 360, integrally connected to a rigid, vertically-oriented hollow tube 362, a flange end 364 which is seated in a correspondingly-shaped recess 366 within the hollow interior of the single element 358. Female receptacle 356 comprises a cavity 368, defined by an upwardly-directed oval-shaped flange 370 in which the plunger 350 reciprocates down and up, respectively, when actuator 360 is actuated and released. The female receptacle 356 comprises a distal passageway 372 and a proximal passageway 374, which communicate one with the other across the single element 358 when the actuator 360 is depressed, by reason of the tear-shaped configuration of the single element 358. Element 358 comprises a 360° reverse bend 376, an annular flange 377, and a pear-shaped lower region, the diameter of which varies so that in the up position, the single element 358 seals passageways 372 and 374 preventing delivery of suction to the interior of the catheter tube 120. Flange 377 is anchored in the assembled position by a retainer 379 which is bonded in the position illustrated in FIG. 2. In the down position, communication of negative pressure between passageways 372 and 374 occurs around a reduced diameter part of the teardrop portion of the element 358. Element 358 also serves to inhibit introduction of atmospheric air into the valve because base plate 354 is sealed in position. Element 358 also serves as its own spring, since the element 358 is stretched in a downward direction as the actuator 360 is depressed. Consequently, the memory of the element 358 causes the single element 358 to be returned to the sealed position illustrated in FIG. 2 when manual force on actuator 360 is released.

Stepped tube 324 comprises exterior annular shoulders upon which medical grade tube may be inserted and retained. Stepped tube 324 defines an interior bore in communication with bore 374 along which negative pressure is communicated selectively, as described above.

Reference is now made to FIG. 4 which illustrates a multiple access apparatus, generally designated 30', which is substantially identical to multiple access system 30 shown and described in connection with FIGS. 1 and 2. Corresponding numerals are used to designate corresponding parts in FIG. 4 which correspond to the parts of FIGS. 1 and 2 and no further description is deemed necessary.

Apparatus 30' differs from apparatus 30 in the provision of an oxygenation catheter cartridge, generally designated 380. Oxygenation catheter cartridge 380 comprises a distal fitting 382. Fitting 382 comprises a hollow male projection 384 through which a hollow oxygenation catheter tube 386 can be manually advanced and retracted into and from a suitable lung position for the purpose of oxygenating and potentially replacing residual carbon dioxide within the selected lung with oxygen. The catheter tube 386 is surrounded by a sheath 388, which is similar in structure and function previously described sheath 304. The distal end of the sheath 388 is held in position by a force-fit collar 390 similar to the way in which collar 306 holds the distal end of sheath 304.

Oxygenation catheter cartridge 380 comprises a proximal fitting 400 which holds in press-fit relation the proximal end of the sheath 388 when a collar 402 is press-fit into the position illustrated in FIG. 4. The trailing fitting 400 is centrally hollow and is in fluid communication with the hollow interior of catheter tube 386. After male projection 384 is press-fit into the hollow interior of barrel 130 and the catheter tube 386 advanced into a desired location within the lungs, valve 404 is manually opened, causing oxygen from source 406 to be delivered at a suitable rate and pressure to the selected lung site.

When utilization of the oxygenation cartridge 380 is over (with the catheter tube 386 retracted) cartridge 380 is removed. Another unused oxygenation catheter cartridge of the same or similar construction could be used later when oxygenation is desired. The same approach is true of cartridge 116, i.e., it can be replaced after one or more uses to prevent undesired risks to the patient due to growth of micro-organisms therein with the passage of time. While the configuration of FIG. 4 has been described in respect to aspirating and oxygenating catheter assemblies, it is to be understood that the configuration will also accommodate use of other catheter assemblies, such as those used for medication, as well as non-catheter access to the respiratory tract of a patient.

Access port 42, along passageway 139, can also be utilized to directly receive lavage and/or medication as illustrated in FIGS. 5 and 6, to which reference is now made. In lieu of plug 160 (not forming a part of the embodiment of FIGS. 5 and 6) a one-piece duck bill valve, generally designated 410, is illustrated as being compression-fit into the proximal or trailing end of barrel 130. Duck bill 410 comprises a trailing radial flange 412, the diameter of which at edge 414 is illustrated as being the same as the outside diameter of wall 138 at edge 136. Flange 412 merges with annular wall 416 and together they define a hollow cylindrical recess defined by surface 418, adapted to receive a lavage or medication receptacle 420, a male projection comprising any of the inserted items described in this specification, being illustrated in FIG. 6 as exemplary. Cylindrical or annular wall 416 also comprises an outside surface 422, the diameter of which is slightly greater than the interior transverse dimension provided by surface 134. Thus, when inserted, duck bill valve 410 remains in place by mason of a radial memory force, outwardly directed, from the duck bill valve 410 against inside surface 134. Accordingly, the duck bill valve 410 is made of a suitable synthetic material with memory, which is substantially yieldable.

Wall 416 merges distally with an inwardly-directed base wall 424, which defines a central opening 426. Radial base wall 424 also merges with duck bill wall segments 428 and 430, which are normally closed where they merge, at site 432. As can be seen from examination of FIG. 6, slit valve 410 is formed of one piece from a suitable elastomeric synthetic resinous material, such as silicone rubber. The nature of the construction of valve 410 is such that passageway 139 is normally closed by valve 410 at site 432. However, Without removal of valve 410, lavage or medication held in container 420 can be introduced into passageway 139 and from thence into the respiratory of the intubated medical patient by causing hollow male projection 434 thereof to be inserted through the opening 426, causing the duck bill wall segments 428 and 430 to part or separate, following which the container 420 can be actuated to discharge the desired amount of medication or lavage. It is to be appreciated that container 420 and male projection 434 are intended to be illustrative and not restrictive. By way of examples on/y, container 420 can be an aerosol container or a container which can be manually collapsed to discharge the appropriate amount of medication or lavage dose. As illustrated, container 420 is sized so as to be snugly received within the hollow defined by annular wall 416. Catheters, probes, and other instruments can also be inserted through valve 410 to accommodate samples, monitoring, inspection, and various forms of respiratory therapy.

The proximal end 526 of the collapsible envelope 500 is illustrated as being bonded to the exterior surface of the fitting 520.

Reference is now made to FIGS. 9 and 10 which illustrate a further multiple access apparatus, generally designated 480, embodying principles in accordance with the present invention. Apparatus 440 comprises a T-shaped, elbow-like housing, generally designated 442, the previously described aspirating catheter assembly 116, permanently assembled with the housing 442, and a second catheter assembly, generally designated 480, also permanently connected with the housing 442.

Elbow fitting 442 comprises a cylindrical wall 444, illustrated as being of uniform thickness and comprising exterior surface 448, interior surface 450 and distal edge 452, which interior surface defines a distal port through which ventilating gases are delivered to the patient, when connected to a tracheal tube, for example.

Elbow fitting 442 also comprises a second proximal barrel 453 comprising a hollow interior into which influent ventilating gases are delivered from a suitable commercially available ventilator. Barrels 444 and 453 are formed as one piece from a suitable synthetic resinous material. The wall 457 comprises a hollow interior defined by an annular interior surface. Wall 457 is preferably of uniform thickness and comprises exterior cylindrical surface 446. The hollow interior of barrel 453 receives ventilating gases from a ventilator and is in open communication with the hollow interior defined by surface 450.

The fitting 442 also comprises a third (second proximal) barrel 456, the interior of which is also hollow and in direct open communication with the hollow interior formed by wall surface 450. A tapered rounded transitional hollow segment 454 connects wall segment 444 with the wall comprising barrel 456. The wall forming barrel 456 comprises an exterior surface 458 and an interior surface 460 (FIG. 10) and terminates in a proximal edge 464. Edge 464 is radially-directed and annular in its configuration, being interrupted by a notch 462, the diametral size of which is selected to accommodate positioning of the transverse tube 122 of the attachment 150 of the aspirating catheter assembly 116 therein. Since catheter assembly 116 has previously been described, no further description in respect to the components thereof as illustrated in FIG. 9 is necessary for an understanding to one of skill in the art, except to reiterate that the distal end of assembly 116 is permanently secured within the female receptacle defined by wall 456, by bonding or the like.

The use of the aspirating catheter assembly 116 and more particularly the catheter tube 120 thereof to aspirate secretions from the lungs of a patient is above-described.

In order to enlarge the number of respiratory access ports available, an additional access port can be readily provided in adapter 442. This may be done by boring or otherwise forming an aperture 470 at the step or transition segment 454 of bell housing 444. While aperture 470 is illustrated as being disposed in a particular diagonal orientation, it is to be appreciated that the direction of aperture 470 in transition wall 454 may be selected, as desired, by those skilled in the art.

The tube 472 having exterior surface 474 the diameter of which is just slightly smaller than aperture 470 is inserted a desired although short distance into the hollow interior formed by wall surface 450 and is cemented, bonded, plastic welded, or otherwise secured in the inserted position, in the manner typified in FIG. 10. The proximal end 482 of the tube 472 is equipped with a female fitting, generally designated 483. Fitting 483 comprises a sleeve 484 bonded or otherwise suitably connected at interface 486 to the proximal end 482 of tube 472. A bell-shaped housing 488 is secured at interface 489 to the sleeve 484, in telescopic bonded or otherwise non-rotatably secured position such that the enlarged region of bell housing 488 defines a female annular groove 490. A second catheter assembly 480 is permanently placed within recess 490, as explained in greater detail hereinafter.

Catheter assembly 480 comprises a distal fitting, generally designated 491, a proximal fitting, generally designated 520, and a catheter tube 512 spanning between the two fittings and encapsulated by a collapsible sheath 500.

Distal fitting 491 comprises a distal collar 496, which is distally tapered at shoulder 497 to form a reduced diameter tip 492. Tip 492 is sized, shaped, and dimensioned so as to accommodate being fit into annular slot 490 and bonded or otherwise permanently secured in that position. Collar 496 comprises an interior cylindrical surface 499 into which a leading end 498 of the collapsible sheath 500 is extended at the proximal end thereof, as illustrated in FIG. 10. A fitting, generally designated 502, is force-fit into the proximal end of the collar 496, being so dimensioned as to hold the distal end 498 of the collapsible sheath 500 in position against inadvertent removal. Fitting 502 comprises a tubular member 504, which has a uniform cylindrical interior surface 505 throughout. The tubular member 504 comprises an outwardly directed radially-extending flange 506 at the proximal end thereof, the flange 506 having a predetermined diameter at annual periphery 507.

A sleeve 508 is force-fit into the proximal end of tubular member 506 (FIG. 10) so that the proximal edge thereof is flush with the proximal edge of flange 507. The interior surface 510 of sleeve 508 defines a cylindrical passageway diametrally sized so as to snugly receive catheter tube 512 in slidable, wiping relation.

A cup-shaped friction lock, generally designated 517, surrounds the catheter tube 512 proximally of fitting 502. Fitting 517 comprises a cylindrical wall 518 which proximally merges with an inwardly-directed radially disposed wall 514. Wall 514 comprises a central aperture 516. The diameter of aperture 516 is substantially the same as the outside diameter of catheter tube 512. Wall 518 comprises an interior annular surface 519, the diameter of which is slightly less than the outside diameter of flange 507. Accordingly, when cup-shaped member 517 is advanced so that surface 519 is superimposed over flange 507, wall 518 is biased outward, which creates a pinching or torque action by wall 514 at aperture 517 upon the exterior surface of tube 512. Thus, when catheter tube 512 has been advanced into the respiratory tract of the patient the desired distance, the location of the distal end of the catheter tube may be preserved in said inserted position by holding the catheter tube 512 in the desired position through collapsible sheath 500 and, also through collapsible sheath 500 advancing the cup-shaped member 517 until it is superimposed at surface 519 over flange 507. Thus, the pinching action of wall 517 at aperture 516 against the exterior surface of the catheter tube 512 will thereafter retain the catheter tube 512 in the predetermined inserted position. In the alternative sleeve 508 can be formed of a compressible material with the outside diameter of sleeve 508 being greater, when unstressed, than the diameter at surface 505. The inside diameter of sleeve 508 at surface 510, when unstressed, can be substantially the same as the outside diameter of catheter tube 512. The catheter tube 512 is inserted to the desired location in the respiratory tract while the sleeve 508 is in the position of FIG. 9. Once the desired indwelling location is reached, the sleeve 508 is advanced along the catheter tube 512 and compression fit into the hollow interior of collar 504, thereby stress or compression reducing both the inside and the outside diameters of sleeve 508. This, in effect, causes sleeve 508 to clamp against the exterior surface of catheter tube 512, holding it in the desired inserted position against inadvertent displacement. The catheter tube 512 may be unclamped simply by removing sleeve 508 from the hollow bore of collar 504.

The distal fitting 520 comprises a female hub having a hollow interior at 521 to which oxygen is communication from source 524 when valve 522 is in the open position.

As illustrated, the proximal end 526 of sheath 500 is bonded, plastic welded, or otherwise suitably secured to the exterior surface 527 of fitting 520. Fitting 520 is hollow so that oxygen supplied to passageway 521 will be communicated along the hollow interior of catheter tube 512 into the respiratory tract of the patient. It is to be appreciated that catheter assembly 480, in lieu of being provided for delivery of oxygen, may be constructed to deliver lavage or medication to the patient as desired using the access site made available by the formation of aperture 470 at step 454 of bell housing 444.

Reference is now made to FIG. 11, which illustrates an additional multi-access respiratory apparatus, generally designated 530, embodying principles of the present invention. Apparatus 530 comprises a Y-adapter, generally designated 532, a medication catheter cartridge or assembly, generally designated 534, and a syringe, generally designated 536, containing a desired form of medication.

Adapter 532 is illustrated as being formed of two separate parts, i.e., distal hollow tubular tip member 538, adapted to be force-fit into a port-defining opening in a tracheal fitting or into a fittingless proximal end of a tracheal tube, which also accommodates patient ventilation. The tapered tip 540 accommodates such insertion, while exterior cylindrical wall surface 542 accommodates the compression fit needed. The proximal end 544 at exterior surface 546 is enlarged so as to snugly be received telescopically in a cylindrically stepped female receptacle 548 at the distal end 550 of the second member 551 of the adapter 532. This union could also be bonded or the like, if desired. Two proximal access passageways 552 and 554 merge into distal passageway 556. Passageway 552 is defined by a bell-shaped housing comprising a relatively small distal annular wall 560, a tapered conical transitional wall section 562, and an enlarged proximal cylindrically-shaped wall portion 564 terminating in a transverse blunt proximal edge 566. The other leg which defines passageway 554 comprises a reduced diameter distal cylindrical wall portion 568, which merges with both Wall segment 560 and wall segment 550. Cylindrical or annular wall 568 also merges with an enlarged cylindrical segment 570 by a diagonally disposed stepped conically-shaped wall portion or angular shoulder 572. The diameter of cylindrical segment 568 comprises a mean diameter substantially similar to the mean diameter of wall segment 560, while wall segment 564 is illustrated as comprising a mean diameter substantially greater than the mean diameter of proximal wall segment 570. However, selection of sizes may be varied in any desired way. While wall segment 564 is adapted to accommodate introduction and exhaustion of ventilating gases, it can also receive a catheter cartridge for aspiration, oxygenation or ventilation, in the manner described above.

While the interior surface of enlarged cylindrical or annular wall surface 570, at 574, is illustrated as sized to receive hollow male distal projection 576 of medication catheter assembly 530 in compression-fit relation, it could be used for ventilation, aspiration, oxygenation, monitoring, or sampling. Male distal projection 576 comprises a cylindrical portion 578 and a tapered tip 580, which defines a spaced aperture 582 through which the medication-delivering catheter tube 584 slidably is displaced.

Wall 578 defines a hollow chamber 585. Wall 576 is diametrally enlarged at shoulder or wall 586, formed as one piece with both wall 576 and enlarged annular wall 588. Annular wall 588 defines a hollow cylindrical region at interior surface 590, into which a catheter wiping washer 592 is positioned. Washer 592 is formed of a suitable synthetic resinous material which is yieldable and defines a central aperture, the diameter of which is slightly less than the outside diameter of catheter tube 584. Thus, when the catheter tube 584 is withdrawn after being advanced through the adapter 532, washer 592 wipes from the exterior surface thereof so that residual substance accumulated thereon is deposited in chamber 585.

Cartridge 534 comprises a collapsible sheath or sleeve 594, which in structure and function is substantially the same as previously described sheath 304.

Double flange fitting 600 functions similar to previously described double flange fitting 292, functioning to hold washer 592 in place, being received in press-fit relation at its distal end within the cylindrically hollow interior of wall 588 at surface 590 and continuously receiving the distal end 596 of the sheath 594 which is compressively held in the assembled position as illustrated in FIG. 11 by a collar 306, as explained previously.

The trailing or proximal end 602 of sheath 594 is secured in compression-fit relation by a second compression ring 306, superimposed over the end 602 which in turn is superimposed over and compressively engages an annulus 604. Annulus 604 comprises a part of a fitting, generally designated 606, which comprises an annular stepped interior member 608, into which a fitting 610 is inserted and secured in the illustrated position of FIG. 11 by bonding agent, adhesive, plastic welding, or in any other suitable way. An enlarged cross-section comprising fitting 606 is illustrated in FIG. 28. The distally extending tubular portion 612 of attachment 610 comprises a bore 614, into which the proximal end 615 of catheter tube 584 is inserted and retained by adhesive, bonding agent, plastic welding, or in any other suitable way.

Member 608 comprises a rearwardly extending annular wall or collar 616, which fits and is retained within a recess 618 of the syringe-receiving proximal luer lock type fitting, generally designated 620. Syringe-receiving proximal fitting 620 comprises a proximal hollow wall 622, which has a forwardly divergent conically tapered interior surface 624, sized and shaped to snugly receive a correspondingly shaped distal tapered hollow end 626 of medication syringe 536, which conventionally comprises a hollow barrel 628 and a plunger 630, the distal end of which comprises an internal piston 631 (FIG. 13). Wall 622 comprises a proximal radially-directed luer flange 632. A cap 634 is provided to removably close the proximal end of wall 622 at flange 632 when syringe 536 is removed to prevent undesired entry of contaminants. Cap 634 is threaded internally at luer threads 636. Cap 634 is rotatably secured to wall 622 by a tether 638 at aperture 640. Accordingly, tether 638 turns at aperture 640 as cap 634 is rotated. The diameter of aperture 640 is less than the diameter of flange 632, but greater than the diameter of wall 622. Thus, the distal end adjacent aperture 640 must be stretched over flange 632, following which it contracts, due to the memory of the synthetic elastomeric material from which tether 638 is formed, to hold the tether at wall 622.

It is to be appreciated that bell housing wall 570 of adapter 532, while being capable of receiving the mediation cartridge 530 and any desired replacement thereof from time to time, can also receive other devices or accessing into or acquiring information concerning the respiratory system of an intubated patient, as mentioned above.

In operation, the catheter assembly or cartridge 530 is inserted at male projection 576 into the female receptacle defined by wall 570 until a firm compression fit is obtained. At the point in time when medication is to be added the cap 634 has been removed and the syringe 536 is inserted as shown in FIG. 11. The catheter tube 584 is advanced through passageway 554 and passageway 556 through the tracheal tube into the respiratory tract of the intubated patient. When the distal tip of the catheter tube 584 is appropriately positioned, the syringe 536, loaded with an appropriate amount and type of medication (at 724–FIG. 13), is implemented by advancing plunger 630 in barrel 628. The medication flows along the flow path defined by the hollow proximal end 626 of the syringe, the hollow interior of fitting 620, the exposed hollow portion of wall 608, the hollow interior of receiving member 610, and through the hollow of the catheter tube 584.

At any desired point in time, the cartridge 520, with the catheter tube 584 retracted, can be manually removed and discarded, following which a fresh cartridge of similar or dissimilar design or purpose can be inserted into the female receptacle defined by wall 570 to assist in providing the appropriate therapy for the patient.

As an example of another access-providing device which may become associated with a female receptacle such as the one defined by wall 570 (FIG. 11), reference is made to FIGS. 7 and 8. In FIGS. 7 and 8, there is illustrated a slit valve device, generally designated 650. Device 650 comprises a hollow chamber defining member, generally designated 652. Chamber defining member 652 is formed as one piece with a tether 654 and slit valve cap 656.

Element 652 comprises a distally-extending annulus 658, which is sized and shaped so as to accommodate being press fitting, for example, into the hollow interior 574 of wall 570 and forcible manual removal therefrom at any desired point. Annulus 658 comprises a beveled leading end 660 and a hollow interior passageway defined by interior annular wall surface 662, illustrated as having a uniform thickness throughout. Annulus 658 merges with transverse or radially directed annular wall 664, which defines a central aperture 666 therein, having a diameter substantially smaller than the diameter defined by wall surface 662. Wall 664 comprises an exposed shoulder 668 adapted to contact the blunt proximal transverse edge 571 of wall 570, for example. Wall 664 merges with an enlarged cylindrical wall 670, which defines a relatively large hollow cylindrically-shaped interior at interior cylindrical surface 672. Wall 670 merges with transverse inwardly-directed radial proximal flange 674, which defines an aperture of desired size at beveled surface 676 to receive the slit valve cap 656, as explained hereinafter in greater detail. Wall 670 is integral with tether 654. While shown as being centrally connected to wall 670, tether 654 can be joined to wall 670 at any other suitable site, such as directly adjacent wall 664. Tether 654 is also integral with a trailing flange 678 of cap 656. Flange 678 comprises an extension 680, which may be manually grasped to remove the slit valve cap 656 from its assembled closed position with member 652, shown in FIG. 8.

Slit valve cap 656, in addition to flange 678 and extension 680 comprises an annular flange 682 comprising beveled edge 683, and a central male projection 684, which contains a central axially-directed slit 686. An annular slot 687 exists between interior surface 688 of wall 682 and exterior surface 690 of male projection 684.

When the slit valve element 656 is displaced from its open position of FIG. 7 to its closed position of FIG. 8, element 656 is press-fit onto the proximal end of member 652, the annular flange 682 compressively engaging wall 670 and male projection 684 forcibly engaging and extending through aperture-defining wall 674 at aperture 676. Male projection terminates in a beveled edge 685. Beveled edges 683 and 685 aid in centering cap 656 as it is force-fit over the proximal end of element 652.

The device 658 when disposed, as explained above in a female receptacle of an adapter, may also be used to removably receive an appropriately sized, shaped, and dimensioned distal end of a catheter assembly of the type described in this specification, when cap 656 is in its open position, shown in FIG. 7. The distal end of the catheter assembly is simply force-fit through aperture 676 into the hollow chamber defined by surface 672 of wall 670 and thereafter used in one of the ways explained above.

In the assembled position, a container 692 of medication or lavage, having a hollow male projection 694 can be manually forced through slit 686 and evacuated in whole or in part to discharge a desired amount of medication or lavage into chamber 672 and thence through the hollow interior of adapter 532 into the respiratory tract of the patient.

Reference is now made to FIGS. 12–16 which illustrate additional configurations embodying principles of the present invention. With reference to FIGS. 12–16, a Y-adapter, generally designated 700, is illustrated. Adapter 700 is similar to adapter 532, previously described in connection with FIG. 11. Those portions of adapter 700 which are the same as adapter 532 have been so numbered and no further description will be provided of these components. One of the differences between adapter 700 and adapter 532 comprises a central reinforcing web 702, illustrated as being planar in configuration, which is located between the two proximal legs or barrels of adapter 700. This adds strength and prevents fracture at the juncture site. An additional difference comprises utilization in adapter 700 of a radial transition wall 704, in lieu of diagonally tapered transition wall 572, to connect cylindrical wall 568 and female receptacle-defining wall 570. Also, the distal male tube of adapter 700 is not stepped, as is the case with adapter 532. Furthermore, the distal end 550 is not internally stepped. Tubular element 538 defines an internal step comprising a shoulder 706, which is exposed just downstream of the merger of passageways 552 and 554. A sleeve 708 is positioned radially in alignment with shoulder 706 and secured by bonding, adhesive, plastic welding or the like around wall 550 to provide strength and reliability and to limit the extent to which tip 540 and tubular wall 538 can be inserted into a female receptacle.

While adapter 700 comprises differences when compared to adapter 532, the objective remains the same, i.e., to provide multiple access capability for treatment, sampling, and monitoring of the respiratory tract of an intubated medical patient. For example, the aspirating catheter cartridge 116, previously described in connection with FIG. 1, can be force-fit or permanently secured into the female receptacle defined by wall 570, as illustrated in FIG. 12, to utilize a negative pressure in the removal of secretion from one or both of the lungs of the patient, in the manner described earlier in this specification. In FIG. 12, the stepped hollow proximal connector 324 of the valve 352 is illustrated as being capped at 710. However, when disposable cartridge 116 is ready for use, cap 710 is manually removed and connection by medical tubing between a source of negative pressure, as explained above, and valve 352 is completed by press-fitting the medical tubing over the exterior shoulders or serrations at hollow male connector 324. It is to be appreciated that while the female receptacle defined by wall 564 of adapter 700 may be dedicated to ventilation, it is still within the scope of the present invention to insert the distal portion of 538/540 of the adapter 700 into a ventilating fitting and utilize the female receptacle defined by wall 564 as an access site for any desired form of therapy, sampling, or monitoring of the patient.

With reference to FIG. 14, the adaptability provided by adapter 700 is further illustrated, i.e., removable or permanent reception in the female receptacle defined by wall 570 of the leading end 576 of the medication cartridge 530, previously described in connection with FIG. 11.

Similarly, the above-described oxygenation cartridge 380 may be temporarily or permanently fit into the hollow interior defined by wall 560 to provide oxygen therapy to the patient, the distal tip 384 of cartridge 380 being shown in FIG. 16 about to be so inserted.

In respect to FIG. 13, a modified form of medication cartridge, generally designated 530' is illustrated in the process of being inserted into a compression fit relationship with the female receptacle defined by wall 560. Medication cartridge 530' is substantially similar to previously described medication cartridge 530 except, the proximal end of the collapsible sheath 594 is illustrated as being held in compression-fit relation by a force-fit collar 720 superimposed over the proximal end of a single, relatively simple tapered fitting 722. Fitting 722 is connected by adhesive or the like to catheter tube 584 to define a common flow path therethrough. The catheter tube 584 and the fitting 722 are, therefore, both hollow and accommodate aligned fluid flow of medication 724 from within the syringe 536 selectively into the patient, in the manner explained earlier in connection with cartridge 530. Cartridge 530' provides the unitary disposable feature explained earlier also in connection with cartridge 530. Distal tip 578 is also illustrated as being equipped with the previously described catheter wash attachment 150.

To improve the quality of health care available to intubated patients, it is important to avoid the possibility that ventilating tubing could be twisted and the availability to the patient of ventilating gases either occluded or materially reduced. To achieve this purpose, the swivel fitting provided by previously described rotatable tubes 88 and 88' are provided. More specifically, bell housings 46 and 80 are typically stationary during use, whereas connector tubes 88 and 88' are readily rotated. Accordingly, when tube 88 is compression or otherwise connected to a tracheal tube, for example, the remainder of adapter 44 may rotate as needed to relieve stress, without risking imposition of torque on the tracheal tube. Similarly, when ventilating tubing is force-fit upon or otherwise connected to tube 88', tube 88' may rotate as needed to relieve stress, prevent twisting of the ventilating tubing, and insure a continuing full supply of ventilating gases to the intubated patient.

It is to be appreciated that while the specific configuration comprising adapter 44, illustrated and described in connection with FIG. 1, comprises a single distal port and a plurality of proximal ports, the swivel feature provided by tubes 88 and 88' may be utilized with any type of ventilating fitting, for example the swivel connection may comprise a tee-piece, an elbow, etc.

Other forms of adapters may comprise elbow configurations which embody principles of the present invention. One elbow configuration is illustrated in FIG. 9, previously described. Another elbow is illustrated in FIG. 17 and is there generally designated 730. Elbow 730 comprises three distinct pieces, i.e., a hollow L-shaped piece, generally designated 732, a proximal rotatable tube, generally designated 734, and a rotatable distal tube 736. Pieces 732, 734, and 736 are formed of suitable synthetic resinous material.

L-shaped member 732 comprises three ports, access port 738, defined by annular wall 740, access port 742, defined by annular wall 744, and access port 746, defined by annular wall 748. As illustrated, port 746 is the largest, port 742 the next largest, and port 738 the smallest.

Annular wall 740 comprises interior and exterior cylindrical surfaces 750 and 752 of uniform diameter, respectively. Wall 740 also comprises a blunt transversely directed edge 754. Wall 740 merges at shoulder 756 with wall 748 and with wall 744 at 90° corner 758.

The interior surface 750 of wall 740 defines a female receptacle into which any of the previously described catheter assemblies or cartridges may be inserted and compression-fit. A monitoring or sampling instrument may also access through port 738. Wall 744 merges with a diametrally enlarged proximal flange 760, which defines a tortuous double open groove 762, comprising two recesses disposed at 90° in respect to each other. The tortuous recess 762 is annular, as is flange 760. Flange 760 extends proximally beyond the proximal edge 764 of wall 744 to accommodate a butt relationship between edge 764 and distal edge 766 of swivel tube 734. The construction of flange 760 accommodates a certain amount of flexibility to accommodate creation of the union illustrated in FIG. 17.

Swivel tube 734 comprises a wall 768 of uniform thickness defined by exterior cylindrical surface 770 and interior cylindrical surface 772. Wall 768 terminates at proximal transverse blunt edge 774 and distal blunt edge 766. Wall 768 also comprises a distal male annulus 776, the double ring configuration of which matches double groove recess 772, there being enough play between male annulus 776 and female receptacle 762 to accommodate relative rotation between tubular element 734 and L-shaped member 732.

It is contemplated that ventilating tubing will be connected to wall 768, for example, by creating a press-fit union therewith so that ventilating gases are delivered to the hollow interior 778 of tubular member 734 to ventilate the patient. The rotatability of wall 768 accommodates the mentioned ready rotation to prevent twisting or otherwise stressing of the ventilating tubing to thereby insure continuous and full delivery of ventilating gases for the full term of such patient therapy.

L-shaped member 732 at the proximal end thereof also comprises previously described flange 760, equipped with double groove tortuous recess 762. The proximal flange 760 is diametrally smaller than the distal flange 760, but the construction is the same.

While distal tubular element 736 is diametrally larger and axially shorter than tubular element 734, the structural makeup is the same and, therefore, element 736 has been identically numbered, requiring no further description. The larger diametral size of element 736 leaves an exposed shoulder at distal edge 764. Accordingly, a distal passageway 780 is provided by swivel tube 736. It is contemplated that the exterior surface 770 will connect, as by a force-fit union with a tracheal tube fitting by which ventilating gases are conveyed to the patient and gases from the patient are exhausted. Also, the hollow interior of L-shaped member 732 in conjunction with the hollow interior of tubular element 736 accommodate passage of monitoring equipment into the patient, as well as catheter tubes for medication, aspiration, and oxygenation, using passageway 738, as explained above.

Reference is now made to FIG. 18 which illustrates a further elbow embodiment or configuration, generally designated 730'. Elbow 730' is of one piece construction, formed from a suitable synthetic resinous material preferably using conventional injection molding techniques. Elbow 730' comprises four access ports 790, 792, 794, and 796. Elbow 730' comprises an annular wall 800, notched at 802 to accommodate a cartridge having a wash tube such as wash tube 122 of attachment 150 of catheter assembly 116, described above. Wall 800 otherwise comprises a blunt proximal edge 804, a smooth cylindrical exterior surface 806, and an interior surface 808, reduced in diameter at shoulder 810. Access port 792 is formed by annular wall 812, which comprises smooth annular exterior and interior surfaces 814 and 816 as well as proximal edge 818. Passageway 792 is in communication with a smaller aperture 820 disposed adjacent shoulder 822. Aperture 820 comprises a lower beveled surface 823 such that medication released under pressure from a container placed in passageway will be deflected, as a spray, toward passageway 796.

Proximal port 794 is formed or defined by an annular wall 822, which comprises a proximal blunt edge 824 illustrated as being radially disposed, a cylindrical interior surface 826, illustrated as being of uniform diameter, and an exterior surface 828, which is divergently tapered in a distal direction. Surface 828 is stepped at diagonal shoulder 830 to provide an enlarged wall thickness at 832 thereby adding strength to the elbow at a point of stress concentration. Previously described aperture 826 is located at the interface between walls 822 and 832, as illustrated in FIG. 18.

Port 796 is defined by an annular wall 834, which comprises a blunt radially-directed distal edge 836, an interior annular surface 838 illustrated as being of uniform diameter, and an exterior surface 840, which is generally annular in its configuration. Wall 834 merges at corner region 842 with enlarged wall segment 832 and at rounded shoulder 844 with wall 800. Wall 800 similarly merges at corner region 846 with enlarged wall segment 832.

It is contemplated that elbow 730' will be connected at wall 822 with ventilating tubing, normally in press-fit relation. It is similarly contemplated that wall 834 will be compression coupled, for example, to a tracheal tube such that ventilating gases delivered to port 794 will pass through port 796 in route to the respiratory tract of the patient.

It is contemplated that the female receptacle defined at interior wall surface 808 of wall 800 will receive in removable, compression-fit relation, any of the previously described catheter assemblies or cartridges by which an aspirating catheter tube, a medication catheter tube, and/or an oxygenation catheter tube can be inserted into the patient through port 796 without discontinuing ventilation. As stated above, it is further contemplated that the female receptacle defined by interior wall surface 816 of wall 812 may receive a medication injecting container such that through activation of the container, for example by use of aerosol techniques or compression of a collapsible container, appropriate lavage and/or medication may be inserted.

It is to be appreciated that the female receptacles defined by wall surfaces 808 and 816 in FIG. 18 as well as the female receptacle defined by wall surface 750 in FIG. 17 may be appropriately capped, for example in the manner described above, during periods of non-use. Similarly, the swivel features shown and described in conjunction with swivel tubes 88 and 88' in FIG. 1 and 734 and 736 in FIG. 7 can be, respectively, combined with the elbow 986. The present invention contemplates providing a swivel feature for either or both main barrels of an elbow fitting, as is illustrated in FIG. 19. FIG. 19 illustrates an elbow, generally designated 850, while elbow 850 can be equipped with the multiple access structural features described above, for simplicity, only two access ports are shown, i.e.. proximal port 852 and distal port 854.

Elbow 850 comprises a central L-shaped passageway throughout defined by wall 856, which is necked down at wall segment 858 and which is enlarged at shoulder 860. Elbow 850 is equipped with a second swivel element 862, which is snap-fit into the hollow interior of proximal end 864 of the associated elbow. The snap-fit union accommodates ready rotation of swivel element 862 in respect to the associated elbow. Any number of snap-fit swivel arrangements can be used, four which are illustrated in FIGS. 20–23.

Figure 20:
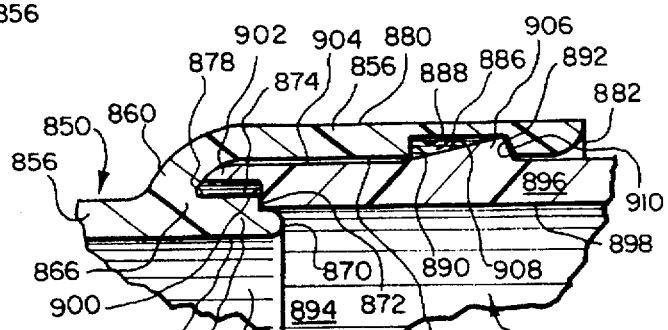
FIG. 20 is an enlarged fragmentary cross-section showing the manner in which the two components of the fitting of FIG. 19 may be united.

FIG. 20 illustrates one specific snap-fit swivel union which may be implemented between elbow 850 and element 862. Wall 856 is illustrated as being bifurcated at location 866 so as to define not only exterior rounded shoulder region 860, but an internal annular wall 868, which is cantilevered proximally from bifurcation site 866. Annular wall 868 comprises a rounded, reduced sized distal edge 870, which merges at annular shoulder 872, with an annular surface 874 wall 868. The interior surface 876 of wall 868 comprises a predetermined diameter. Shoulder 872 functions in the capacity of a thrust bearing, as explained hereinafter. Diametrically enlarged wall 856 is radially spaced from wall 868 so as to define a tapered slot 878 therebetween. Wall 856, distal of rounded shoulder 860 comprises an exterior surface 880, illustrated as being of uniform diameter throughout. Wall 856 terminates in rounded proximal tip 882.

The interior surface 884 of wall 856 is discontinuous, defining an annular recess 886. Recess 886 comprises a longitudinally extending interior surface 888 of predetermined axial length, flanked by a radially-directed proximal shoulder 890 and a diagonally disposed distal shoulder 892.

The element 862 comprises a hollow interior 894, disposed within a surrounding wall 896, the interior surface 898 of which defines passageway 894.

The proximal portion of wall 896 comprises a generally transversely directed shoulder 900, intended to contiguously contact thrust bearing shoulder 870 so as to accommodate rotation of element 862 in respect to elbow 850. Shoulder 900 merges with a tapered sealing tip 902. Tip 902 is yieldable in a radially direction so that, upon contact with interior surface 884 within slot 878, tip 902 is deflected radially inwardly thereby forming a seal between tip 902 and the surface 884 transitional segment 860. The extent of such deflection by tip 902 is controlled by the dimensional relationship between shoulders 872 and 900. The exterior surface 904 of wall 896 is radially enlarged at wedge-shaped annular ring 906. Wedge-shaped annular ring 906 is defined by intersecting diagonal surfaces 908 and 910. The maximum diameter of wedge-shaped annulus 906 is slightly less than the diameter of surface 888. The nature of the synthetic resinous material from which element 862 is formed and the shape of element 862 accommodate deflection during insertion of element 862 into the hollow interior of the proximal end 864 of elbow 850. More specifically, wall 896 is caused to be inwardly radially deflected as diagonal wall 809 rides downwardly along surface 882, which continues until wedge-shaped annulus 906 is aligned with recess 886, at which time the memory of the material from which wall 896 is made causes the wedge-shaped annulus 908 to radially expand into the position illustrated in FIG. 20, with diagonal surface 910 directly juxtaposed surface 892.

The inter-relationship of wedge-shaped annulus 906 and recess 886 accommodate ease of rotation of element 862 in respect to elbow 850 as needed to prevent twisting of ventilation tubing or the like. At the same time, the flexible tip 902 creates a seal with the interior surface of transitional wall segment 960, preventing entry of atmospheric gases or debris along the interface between element 862 and elbow 850. Shoulders 872 and 900 limit the distal displacement of element 862 in relationship to elbow 850, while juxtaposed surfaces 892 and 910 limit the displacement which can be accommodated between element 862 and 850 in a proximal direction.

Figure 21:
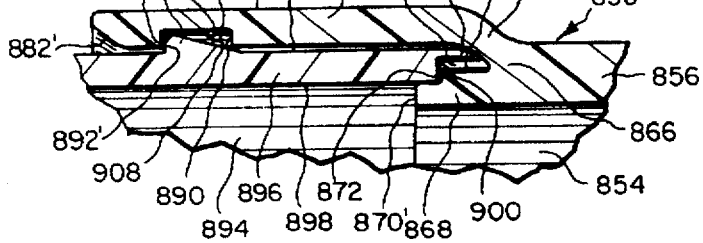
FIG. 21 is an enlarged fragmentary cross-section of one more way in which the two components of the adapter of FIG. 19 may be joined one to the other.

A similar arrangement as illustrated and described in conjunction with FIG. 20 is presented in FIG. 21, the primarily differences comprising (a) a primarily blunt edge 870' in lieu of rounded edge 870, (b) an annular groove 886' wherein recesses surface 892' replaces surface 906 and is disposed radially as opposed to diagonally, (c) radially disposed wedge surface 110' in lieu of wedge surface 910; and (d) at proximal bell housing end 864, proximal beveled edge 882' replaces rounded edge 882. Otherwise the structure is the same as is illustrated in FIG. 20 and is so numerically designated. The operation or functional aspects of the embodiment of FIG. 21 are essentially the same as those explained above in conjunction with FIG. 20.

Figure 22:
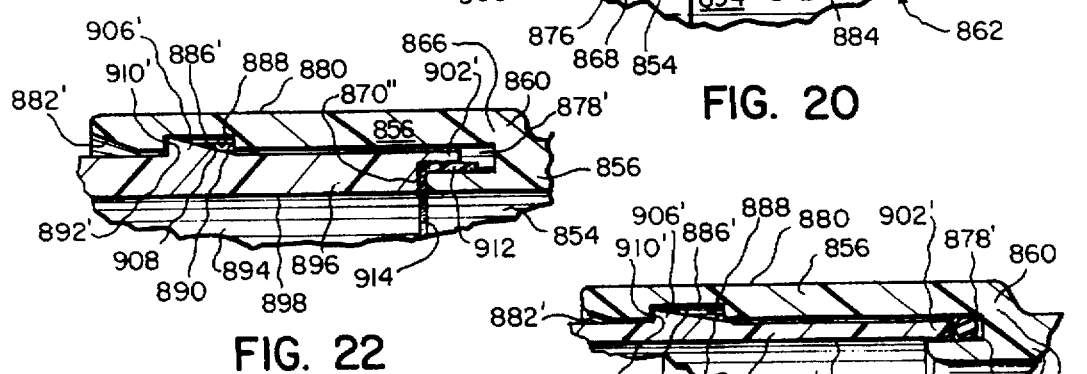
FIG. 22 is an enlarged fragmentary cross-section of still another way in which the two components of the adapter of FIG. 19 may be united.

The snap-fit arrangement of FIG. 22 is similar to the one illustrated in FIG. 21, except (a) shoulder 872 is eliminated, (b) tapered recess 878 is replaced by a rectangulafiy-shaped recess 878', (c) the yieldable sealing tip 902 is eliminated, and (d) the rectangularly-shaped non-deflectable tip 902' is used to replace tip 902, and (e) a seal 912 is included. Further, the wall 896 and shoulder 870" are caused to be substantially aligned with rather than offset in respect to the wall 868. Seal 912 is interposed at site 914. Seal 912 serves to accommodate ease of rotation of element 862 in respect to elbow 850 while sealing the interface 914 against entry of atmospheric materials between the element 862 and the elbow 850. Otherwise the function of the embodiment of FIG. 22 is substantially the same as the embodiments described above concerning FIGS. 20 and 21. Seal 912 can be a strip of teflon (polytetrafiuoroethylene) or a bead of extruded sealant, such as medical grade silicone gel.

Figure 23:
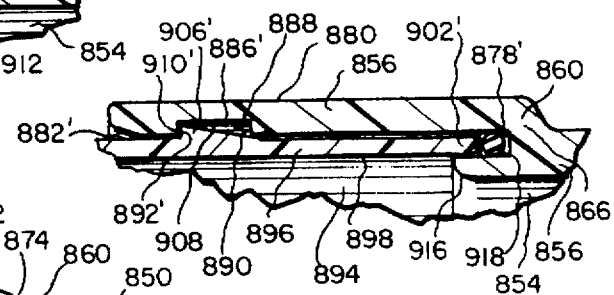
FIG. 23 is an enlarged fragmentary cross-section of still a further way in which the two components of the adapter of FIG. 19 may be joined.

The snap, rotation-accommodating union between elbow 850 and element 862 illustrated in FIG. 23 is substantially similar to embodiment of FIG. 22 except (a) rectangular edge 870" is replaced by rounded offset edge 916, (b) the seal 912 is eliminated, and (c) a Suitably sized O-ring 918 is placed in recess 878' to seal against entry of atmospheric materials between the overlapped areas of element 862 and elbow 850. The function of the union between elbow 850 and element 862 is essentially the same as mentioned above.

In any of the catheter cartridges forming a part of the present invention, it may be desirable, once the catheter tube is inserted a given distance to a predetermined location within the respiratory tract of the patient, to lock the catheter tube releasibly into the inserted position to prevent inadvertent displacement of the distal tip of the catheter tube fore or aft. Such displacement, if it occurs, can be either injurious to the patient or render less effective the therapy being administered. In this regard and as an example only, reference is made to FIGS. 24-27, which illustrate a further releasible catheter tube lock mechanism. The lock mechanism, generally designated 930, is mounted at the distal end of a catheter tube cartridge. While not illustrated, the proximal end of catheter cartridge or assembly 930 may be any one of the proximal ends of any catheter assembly described above. In any event, cartridge 930 comprises a hollow catheter tube 932 disposed in a collapsible plastic sheath or tube 934 and secured by a compression fit, i.e., by superimposing the proximal end 936 over an outside ring 938 of a distal fitting, generally designated 940 and forcing a collar 306 over end 936, as explained above.

Fitting 940 comprises a generally rectangular body segment 942 in which is fashioned a rectangular slot 944. Slot 944 is illustrated as being oriented in a vertical direction and as being open at the top and bottom thereof. Slot 944 is sized and shaped so as to snugly receive a slider actuation plate 946 to thereby accommodate upward and downward movement. Plate 946 comprises a pair of ears 948 at one end thereof, which collectively provide a transverse dimension to slider plate 946 which exceeds the transverse dimension of slot 944. This prevents slider plate 944 from, at any time, particularly during the assembly process, to fall completely through the slot 944. The snugness between plate 946 and slot 944 is such as to normally retain the plate 946 in any manually derived position desired.

Plate 946 comprises a key hole opening 950 disposed at the center thereof. During initial assembly, the slider plate is placed in its downward most position, as illustrated in FIG. 26, and the catheter tube 932 is displaced loosely through the enlarged portion 952 of the key hole aperture 950. When in this position, the user may slide the catheter tube 932 back and forth through the slider plate 946 in an unrestrained position. However, when the catheter tube 932 is inserted to the desired length and correctly positioned within the respiratory tract of the medical patient, the slider plate may be lifted manually from the position of FIG. 26 to that of FIG. 25, forcing the catheter tube into the narrow portion 954 of the key hole opening 950. This step partially collapses the catheter tube 932, causing the catheter tube 932 to be compressively restrained against inadvertent displacement from the desired inserted position.

The slotted body 942 is secured by adhesive, bonding agent, plastic welding or the like at interface 956 to a distal housing, generally designated 958. Tip housing 958 comprises a trailing radially-directed flange 960, which comprises a trailing surface 962 and merges with a cylindrical wall portion 964 at corner 966. Cylindrical wall 964 defines a hollow interior or chamber 968, through which catheter tube 932 is manually reciprocated as and when desired. Wall 964 merges with a rounded tip 970, which defines an axially disposed aperture 972 through which catheter tube 932 also reciprocates. A catheter wiping washer 974 is firmly compressively held between surface 962 of housing 958 and surface 976 of fitting 940. A central aperture 978 is sized so as to compressively engage and wipe surface debris from the exterior of the catheter tube 932, when and as it is withdrawn from the respiratory tract of a patient.

Figure 29:
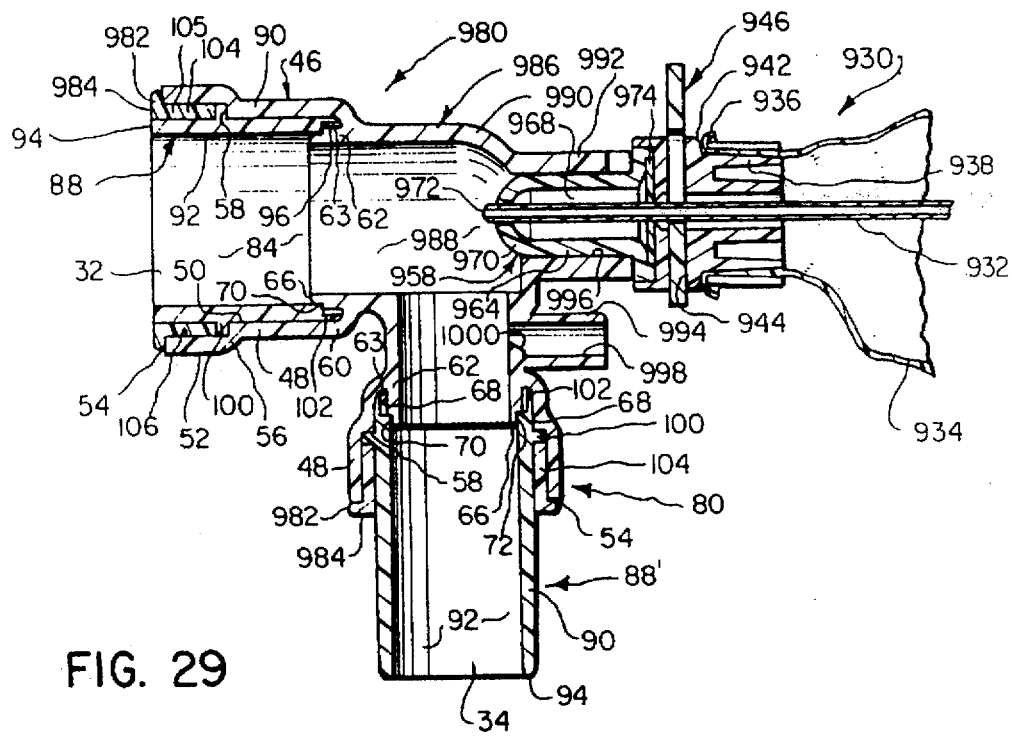
FIG. 29 is an enlarged fragmentary cross-section of a further elbow configuration of the present invention, comprising the swivel ventilating connectors of FIG. 1 combined with a unitized catheter assembly or cartridge.

Reference is now made to FIG. 29 which illustrates a further elbow type connector or adapter, generally designated 980. Adapter 980 has two swivel ends constructed substantially the same as to the two swivel ends 46 and 80. Corresponding numerals are used in FIG. 29 for parts which are substantially the same as those illustrated in FIG. 1 and previously described concerning the swivel portions. The only significant difference comprises the use of a flange 982 at the exposed end of collar 104 in each swivel assembly. Flange 982 rotatably abuts bell housing blunt edge 54 to provide improved aligned rotation of the collar 90 in respect to the bell housing 46. Collar 90 also extends beyond blunt edge 54 so as to be flush with the exposed edge 984 of the flange 982.

Swivel segment 49 of the adapter 980 in FIG. 29 is intended to facilitate connection to a tracheal tube, whereas the swivel connector 80, disposed at essentially 90° to swivel connector 46 is intended to facilitate connection to ventilating tubing in the manner for purposes earlier described. The bell housings of swivel connectors 46 and 80 integrally merge with an L-shaped segment, generally designated 986 to provide an L-shaped passageway through the adapter 980. The hollow portion of L-shaped segment 986 is designated 988. The wall 990 forming L-shaped segment 986 urges into two cylindrical segments 992 and 994 which respectively define proximal access ports 996 and 998. Access port 998 comprises a distal diagonal wall 1000, which functions as a deflector so that discharge medication, container placed in port 9 and 98 is caused to strike deflector surface 1000 and to thereby be re-directed toward distal port 32 of adapter 980.

Port 996 is sized and shaped so as to accommodate receipt of any of the previously described catheter assemblies or cartridges, the cartridge configuration of FIG. 24 being illustrated as having been disposed in port 996, at the distal end thereof. Since the catheter assembly of FIG. 24 was previously described, no further comments are necessary.

Figure 30:
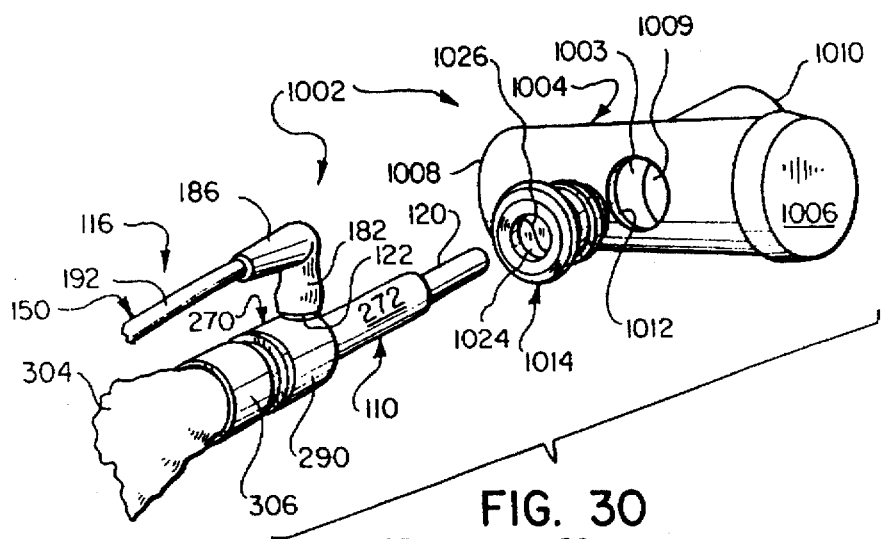
FIG. 30 is an exploded fragmentary perspective of a quick change adapter, slit valve and catheter assembly configuration embodying principles of the present invention.
Figure 31:
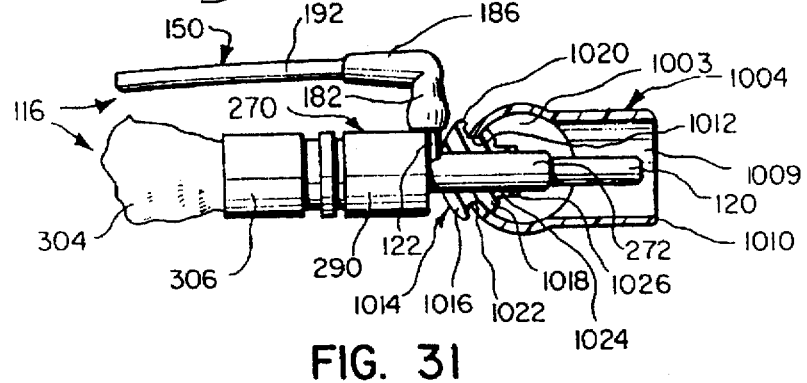
FIG. 31 is a cross-section taken along lines 31—31 of FIG. 30 with the components in their assembled condition.

Reference is now made to FIGS. 30 and 31 which illustrate a further respiratory access apparatus, generally designated 1002; embodying principles in accordance with the present invention. Access apparatus 1002 comprises a T-shaped adapter, generally designated 1004, which is hollow and provides four access ports, i.e., a first access port closed by a removable cap 1006, a proximal ventilating port 1003 which commences at an edge 1008, a distal ventilating port 1009, which ends at edge 1010, and an aperture 1012, which is in alignment with the distal ventilating port 1009.

A slit valve mechanism, generally designated 1014, is force-fit into aperture 1012 to create a normally closed access port, as illustrated in FIG. 31. Slit valve mechanism 1014 comprises an annular body of material, which comprises an interior and exterior flange 1018 and 1020, the respective diameters of which are materially greater than the diameter of aperture 1012. An annular recess 1022 is located between annular flanges 1018 and 1020, the diameter of which is slightly greater than the diameter of aperture 1012. The material from which slit valve mechanism 1014 is formed is extremely pliant, such as silicone rubber, so that it may be manually deformed to achieve the position of FIG. 31.

In the unstressed state, slit valve mechanism 1014 comprises a central diaphragm 1024, which is thin and deformable. An S-shaped slit 1026 extends axially through the diaphragm 1024. Other slit configurations could be used, as could a plurality of slits.

In the unstressed condition of FIG. 30 or in the condition of FIG. 31 after insertion into aperture 1012, but before being penetrated by the distal end of a catheter assembly, for example, diaphragm 1024 extends transversely across the slit valve mechanism 1014 and slit 1026 is closed, preventing entry of atmospheric gases and other materials into the T-shaped adapter 1004 through either aperture 1012 or slit valve mechanism 1014. However, when the slit valve mechanism 1014 is penetrated by the distal end of any one of the catheter cartridges or assemblies described above, such as aspirating catheter assembly 116, which is illustrated in FIGS. 30 and 31, the diaphragm yields and slit 1026 is open and the diaphragm 1024 is deflected through approximately 90°, as illustrated in FIG. 31 so as to accommodate not only entry of the distal end of the catheter assembly 116, but press-fit retention thereof as illustrated in FIG. 31 due to the memory of the material from which slit valve mechanism 1014 is formed.

When the aspirating catheter or other therapy is complete, the health care provider simply manually grasps the catheter assembly or the like and withdraws the same from the slit valve mechanism 1014. The catheter assembly may then be discarded. Upon withdrawal, the diaphragm 124 returns to its radial orientation and the two lips of the S-shaped slit 1026 closed in edge-to-edge relation, returning the slit valve mechanism 1014 to its normally closed position.

Figure 32:
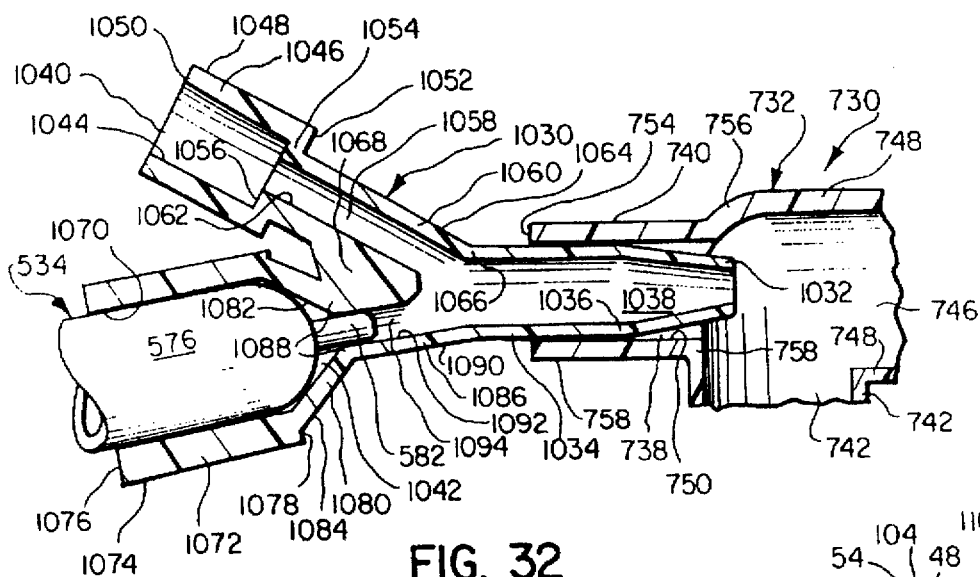
FIG. 32 is an enlarged fragmentary cross-section of a further embodiment of the invention comprising an elbow, an adapter and a catheter assembly.

To facilitate a tandem relationship between adapters to implement principles of the present invention thereby enhancing access to the respiratory tract, reference is now made to FIGS. 32–36. Previously described elbow type adapter 732, comprising a hollow L-shaped member is illustrated in FIG. 32 as accommodating receipt of the distal end of a Y adapter, generally designated 1030, in passageway 738 and defined by the interior surface 75 of cylindrical wall 740.

Y adapter 1030 is illustrated as being formed as one piece from suitable synthetic resinous material so as to comprise a tapered distal tip 1032 and a cylindrical wall 1034 with which the tip 1032 merges at annular site 1036. Together, tip 1032 and cylindrical distal wall 1034 define a hollow distal passageway 1038 through which multiple port access to single elbow port 746 is provided, and from thence to the respiratory tract of an intubated medical patient.

Two proximal ports 1040 and 1042 are provided by Y adapter 1030. Port 1040 is formed by interior cylindrical surface 1044, forming a part of cylindrical wall 1046. Wall 1046 comprises an exterior surface 1048, a proximal radially-directed blunt edge 1050, and a diameter-reducing shoulder 1052. Shoulder 1052 forms a part of an inwardly-directed radial wall 1054, which comprises an interior shoulder 1056. Passageway 1040 merges with a diametrally reduced passageway 1058 disposed within the hollow interior of wall 1060. Wall 1060 comprises an interior cylindrical surface 1062, defining the diameter of passageway 1058 and an exterior surface 1064. Wall 1060 merges with wall 1034 at annular site 1066. Passageway 1058 merges with passageway 1038 generally within site 1066. Wall 1060 also merges with wall 1054 and with a reinforcing web 1068, which enhances the strength of Y adapter 1030.

Port 1042 is defined primarily by interior surface 1070 of wall 1072, which also comprises an exterior surface 1074, a proximal radially-directed edge 1076 and a distal shoulder 1078. Wall 1072 merges adjacent shoulder 1078 with a conically-shaped tapered wall 1080. Wall 1080 comprises an interior surface 1082 and an exterior surface 1084. Wall 1080 merges with reinforcing web 1068 and with the cylindrically-shaped wall portion 1086 at corner site 1088. Wall portion 1086 comprises an exterior surface 1090 and an interior surface 1092. Wall portion 1086 also merges with wall 1034 and wall 1060 at annular site 1066.

Thus, passageway 1042 is juxtaposed and aligned with a reduced diameter passageway 1094. Passageway 1094 merges with passageways 1038 and 1058 adjacent corner 1066.

It is to be appreciated that the apparatus of FIG. 32 converts, in effect, the single access port 750 to two access ports, i.e., ports 1040 and 1042 by utilization of adapter 1030. Access ports 1040 and 1042 accommodate reception of the proximal end of any of the catheter assemblies heretofore described, such as catheter assembly 534, illustrated as being compression fit into port 1042 at surface 1070, in FIG. 32. Access ports 1040 and 1042 may also be used to monitor and to obtain samples from the respiratory tract of an intubated patient.

Figure 33:
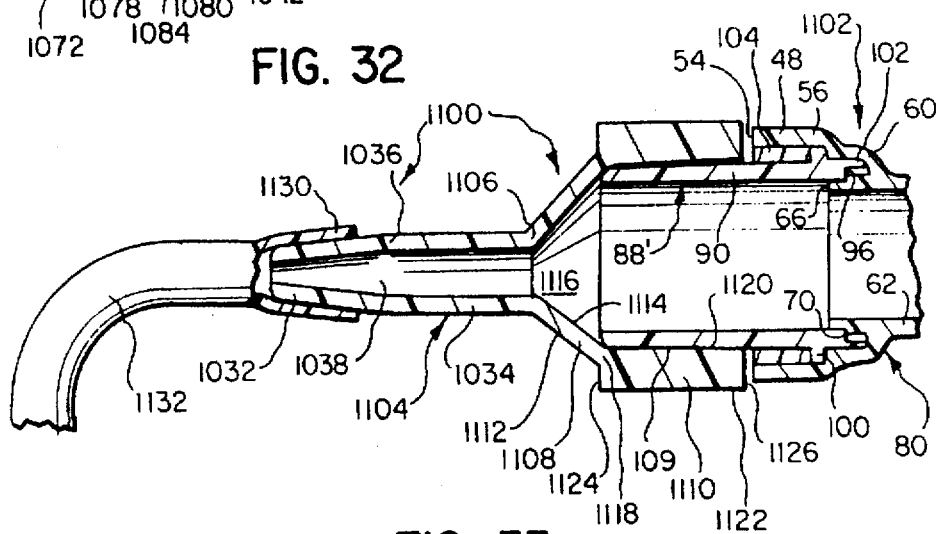
FIG. 33 is an enlarged fragmentary cross-section of still another embodiment of the present invention comprising a fittingless tracheal tube, a first adapter and a second adapter.

Reference is now made specifically to FIG. 33, which illustrates a multiple adapter configuration, generally designated 1100, by which a connection can be made to the exposed end of an indwelling tracheal tube having no fitting.

Specifically, swivel connector 80 is illustrated in FIG. 33 as being placed at the distal end of an adapter, generally designated 1102. Since swivel connector 80 has previously been described, no further description is necessary. Swivel connector 80 is telescopically joined to an enlarged end of a funnel-shaped adapter, generally designated 1104. The distal end of fitting 1104 is identical to the distal end of fitting 1030, described above in connection with FIG. 32. The distal end of fitting 1104 has been enumerated in FIG. 33 as in FIG. 32, requiring no further description of that portion of adapter 1104. Cylindrical wall 1034 merges at annular site 1106 with a conically-shaped, diagonally-directed wall 1108 which merges proximally with and forms a transitional section to enlarged cylindrical wall 1110. Wall 1108 comprises an exterior surface 1112 and an interior surface 1114, the thickness of wall 1108 being illustrated as being substantially uniform throughout its length. Passageway 1038 contained within tip 1032 and wall 1034 merges with hollow conically-shaped chamber 1116 disposed interior of wall 1108.

Wall 1108 merges at corner site 1118 with cylindrical wall 1110. Cylindrical wall 110 comprises an interior cylindrical surface 1120, an exterior cylindrical surface 1122, a distal shoulder 1124 (adjacent corner 1118), and a proximal shoulder 1126. The interior diameter of surface 1120 can be slightly tapered and is sized so as to receive the outside surface 109 of wall 90 of swivel connector 80 in press-fit relation.

The tip 1032 of adapter 1104 is illustrated as being press-fit into the exposed distal end 1130 of indwelling tracheal tube 1132 so as to enlarge said distal end 1130 thereby creating a compression fit between tip 1032 and distal end 1130. In this way, the need for an exposed fitting at the end 1130 of tracheal tube 1132 is eliminated, without compromise of patient safety and well-being.

In lieu of the single access port adapter 1104, a multiple access port adapter, such as adapter 1030, illustrated in FIG. 32, could be used between the fittingless tracheal tube end 1130 and a second adapter, such as adapter 1102.

Reference is now made to FIG. 34 which illustrates an additional manner in which the number of access ports available to the respiratory tract of an intubated medical patient can be enlarged through use in tandem of an elbow and a multiple part Y adapter. More specifically, the multiple access apparatus of FIG. 34, generally designated 1140, is illustrated as comprising previously described elbow adapter 986 and the second adapter, generally designated 1142, which comprises an adaptation of adapter 44 illustrated in FIG. 1 and described earlier in connection with FIG. 1. Adapter 1142 eliminates proximal swivel connector 80, replacing it with the solid wall closing annular site 82 and also eliminates distal swivel connector 46. Otherwise, adapter 1142 is constructed and functions as heretofore described in respect to adapter 44 and is so enumerated in FIG. 34. No further description is necessary, other than to point out that ventilation occurs in apparatus 1140 of FIG. 34 through elbow adapter 986, making elimination of swivel connectors 46 and 80 feasible and advisable.

Cylindrical wall 62 is sized and constructed so as to comprise a distal edge 1144 and to present a diameter at surface 69 which accommodates a press-fit union against wall 996 comprising the interior surface of cylindrical wall 968. A conically-shaped hollow transition wall segment 1143 extends from annular wall site 1145 to annular wall site 1147 thereby connecting wall 62 to walls 112 and 138, respectively.

Accordingly, the single proximal access port defined by surface 996 is, in effect, increased four-fold by utilization of adapter 1142, which provides proximal access ports 36, 38, 40, and 42, as explained earlier.

Reference is now made to FIG. 35 which illustrates apparatus 1149, which demonstrates the manner in which one port of a cross-adapter, generally designated 1150, can be united with the adapter 1142 described above in connection with FIG. 34 to multiply the number of access ports available to sample, monitor, and provide therapy in the respiratory tract of an intubated medical patient. Specifically, cross-adapter 1150 is illustrated as comprising four hollow barrels 1152, 1154, 1156, and 1158, each barrel comprising a relatively thin cylindrical wall, such as cylindrical walls 1160 and 1162, respectively, by which a hollow interior passageway or port is defined, such as ports 1164 and 1166, respectively, defined by cylindrical interior surfaces 1168 and 1170. The port within barrel 1156 is illustrated as being capped at cap 1172. Cap 1172 may be press-fit into position so as to be manually removable, when and if desired. In the illustrated configuration, the port within barrel 1154 may be connected to a tracheal tube, while port 1164 is connected to a source of ventilation. Accordingly, port 1166 is available to straight line monitor, sample and to introduce selectively a catheter tube to aspirate, oxygenate, or medicare, in the manner described above. In addition, lavage can be added when and if desired through port 1166. By simply inserting distal end at wall 62 of adapter 1142 (described in conjunction with FIG. 34) into compression-fit relation within port 1166 at wall surface 1170, the single port 1166 may be used to facilitate use of the four proximal access ports 36, 38, 40, and 42 of adapter 1142, in the manner described above.

Reference is now made to FIG. 36, which illustrates a further multiple access apparatus generally designated 1180, in accordance with the present invention. Apparatus 1180 comprises a first Y adapter, generally designated 1182, and adapter 1142 described earlier in conjunction with FIG. 34. Adapter 1182 comprises, in combination, previously described swivel connectors 46 and 80 of the adapter 44, previously described in connection with FIG. 1. Proximal barrels 110 and 130 of adapter 44 are eliminated in adapter 1182 and wall 62 is cylindrically extended to a predetermined distance ending in proximal edge 1184. Thus, extended wall 62 defines a proximal port 1186 defined by interior surface 64 adjacent edge 1184. By properly sizing and shaping the distal end of adapter 1142, the same may be press-fit telescopically into the passageway 1186 so as to firmly compressively engage interior wall surface 64 to thereby provide for access through any of the ports 36, 38, 40, and 42 of adapter 1142 monitoring, sampling, and therapy, using the one proximal port 1186 of adapter 1182.

Figure 37:
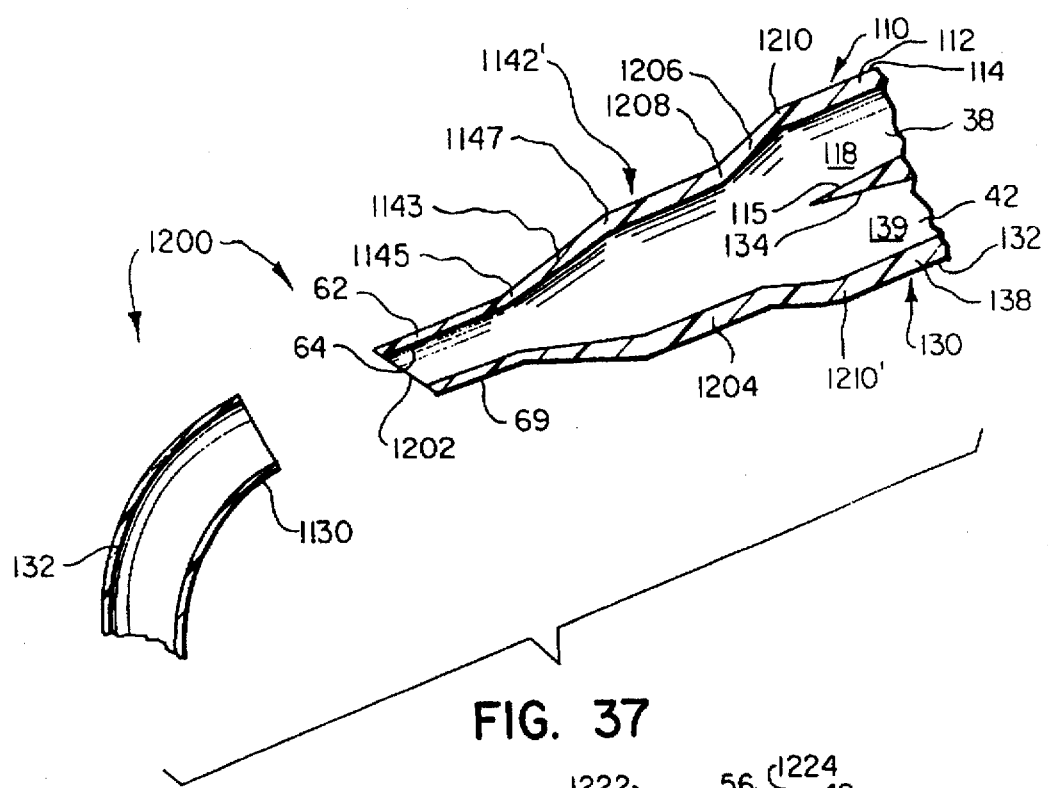
FIG. 37 is an additional cross-section of a further adapter embodiment of the invention.

Reference is now made to FIG. 37, which illustrates an additional multiple access apparatus, generally designated 1200, embodying principles of the present invention and providing for direct connection to a fittingless tracheal tube. More specifically, apparatus 1200 is illustrated as comprising previously described tracheal tube 1132 which comprises an exposed fittingless proximal end 1130. The distal end of the tracheal tube 1132 of FIG. 37 is understood to be disposed indwelling in the respiratory tract of an intubated medical patient.

Apparatus 1200 is illustrated as comprising adapter 1142' which is a slight variation of previously described adapter 1142. To the extent adapter 1142' comprises the same elements as adapter 1142 these elements are correspondingly enumerated in FIG. 37 and no further description is needed. The differences will now be described. Adapter 1142' comprises a beveled leading edge 1202 in lieu of one transverse edge 1144 previously described in respect to adapter 1142. The beveled edge 1202 makes it easier to insert the distal end of adapter 1142' into the proximal end 1130 of the tracheal tube 1132 so as to enlarge it thereby creating and retaining a telescopic connection by a compression fit.

Adapter 1142', as illustrated, also comprises, when compared with previously described adapter 1142 an additional cylindrical wall section 1204, which is centrally hollow and an additional stepped or diagonally-directed conically-shaped wall 1206 which is also hollow. Wall sections 1204 and 1206 are serially disposed between the conically-shaped wall segment 1143 and the proximal walls 112 and 138, respectively. Cylindrical hollow wall 1204 joins conical hollow wall segment 1206 at annular wall site 1208 and conical wall 1206 joins hollow wall segments 112 and 138 at annular wall site 1210.

Figure 38:
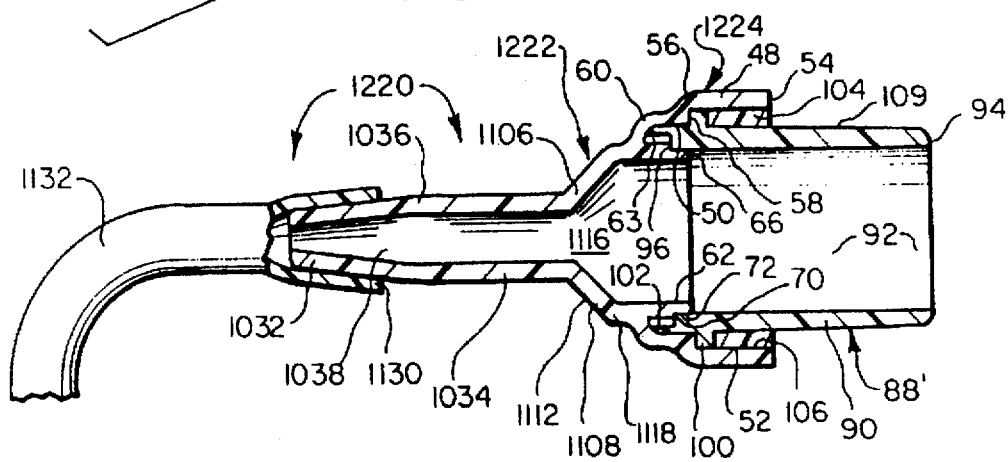
FIG. 38 is a cross-section of a tracheal tube equipped with a swivel proximal fitting.

Reference is now made to FIG. 38 which illustrates a further multiple access apparatus, generally designated 1220, embodying principles of the present invention by which the number of access sites to the respiratory tract of an intubated patient may be enlarged. Apparatus 1220 is illustrated as comprising previously described tracheal tube 1132, which comprises the previously described proximal end 1130 into which a funnel-shaped adapter, generally designated 1222 has been force-fit at its distal end or tip 1032. Since adapter 1222 between tip 1032 and annular site 1118 is identical to the corresponding portion of adapter 1222, the same numerals have been used in FIG. 38 and any further description thereof is not necessary to impart an understanding to those skilled in the art.

Conical wall segment 1108 of adapter 1222 merges at annular site 1118 with a bell-shaped housing, generally designated 1224, the structure of which is substantially identical to previously described bell-shaped housing 80. Accordingly, bell housing 1224 has been enumerated identically to the enumeration in FIG. 1 of bell housing 80 and no further description is necessary for those skilled in the art.

Adapter 1222 also comprises previously described swivel connecting tube 88', earlier described in conjunction with FIG. 1. Swivel tube 88' is rotatably seated and retained by the bell-shaped housing 1222, in the manner heretofore explained in connection with swivel tube 88' in FIG. 1. It is to be appreciated that while a source of ventilation can be directly connected to swivel tube 88', so too can an adapter comprising a plurality of proximal access ports of the type explained above.

The invention may be embodied in other specific forms without departing from the spirit of essential characteristics thereof. The present embodiments therefore to be considered in all respects as illustrative and are not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for selectively providing a plurality of different types of respiratory therapies in combination with an endotracheal tube, said method comprising the steps of:

providing an adapter means adapted for connection to an end of an endotracheal tube, said adapter means comprising a pair of connection ports, at least one of said ports being adapted for connection to a ventilator means;

providing a plurality of interchangeable catheter cartridge means for providing any one of several desired types of respiratory therapies including:

first catheter cartridge means for aspirating fluids therethrough, adapted for connection to a source of vacuum, and comprising an aspirating catheter enclosed within a collapsible sheath, first connector means for selective, releasable fluid-tight connection to one of said ports of said adapter means, an integral wash chamber formed in said first connector means, liquid introduction means for carrying liquid directly from a liquid dispensing container into said integral wash chamber without passing through said adapter means, second connector means adapted for fluid-tight connection to a source of vacuum, and valve means in fluid communication with said aspirating catheter and operable to selectively place said aspirating catheter and an endotracheal tube in communication with a source of vacuum to effect aspiration of fluids therethrough; and second catheter cartridge means for delivery of fluid through an endotracheal tube and comprising a fluid delivery catheter enclosed within a collapsible sheath, first connector means for selective, releasable fluid-tight connection to said one of said ports of said adapter means so as to be selectively interchangeable with said first catheter cartridge means, and second connector means for fluid-tight connection to a source of fluid to be delivered;

connecting one of said plurality of catheter cartridge means with said adapter means to form a first connection assembly; and disconnecting said one of said plurality of catheter cartridge means from said adapter means and connecting another of said plurality of catheter cartridge means with said adapter means to form a second connection assembly.

2. A method as recited in claim 1, further including the steps of providing a third catheter cartridge means for providing an additional type of respiratory therapy and selectively connecting said third catheter cartridge means with said adaptor means.

3. A method as recited in claim 1, wherein said adapter means provides a non-swiveling connection to an endotracheal tube.

4. A method as recited in claim 1, wherein said adapter means is provided from one of a plurality of adapters, each sized for connection to a complementary sized endotracheal tube.

5. A method as recited in claim 1, wherein said adapter means comprises a Y-adapter having an elongated distal end adapted for press fit connection inside an end of an endotracheal tube.

6. A method as recited in claim 1, wherein said adapter means comprises a Y-adapter for connection to an end of an endotracheal tube, said Y-adapter including a distal fitting adapted for connection to an endotracheal tube, a first proximal fitting adapted for connection to a ventilator means, and a second proximal fitting, said first and second proximal fittings of said Y-adapter comprising said pair of connection ports of said adapter means.

7. A method as recited in claim 6, wherein said first catheter cartridge means comprises a first catheter cartridge including said aspirating catheter enclosed within said collapsible sheath, a first connector for selective, releasable fluid-tight connection to said second proximal fitting of said Y-adapter, an integral wash chamber formed in said first connector surrounding a portion of said aspirating catheter, a liquid introduction assembly that carries liquid directly from a liquid dispensing container into said integral wash chamber without passing through said Y-adapter, a second connector adapted for fluid-tight connection to a source of vacuum, and said valve means.

8. A method as recited in claim 6, wherein said second catheter cartridge means comprises a second catheter cartridge including said fluid delivery catheter enclosed within said collapsible sheath, a first connector for selective, releasable fluid-tight connection to said second proximal fitting of said Y-adapter so as to be selectively interchangeable with said first catheter cartridge, and a second connector for said fluid-tight connection to a source of fluid to be delivered.

9. A method as recited in claim 1, wherein said liquid introduction means comprises tubing, connected directly to said first connector means, and proximal fitting means adapted for connection to said liquid dispensing container.

10. A method as recited in claim 9, wherein said proximal fitting means comprises valve means to seal said liquid introduction means when said liquid dispensing container is not attached thereto.

11. A method as recited in claim 1, wherein said second connector means of said second catheter cartridge means comprises a luer connection adapted for connection to a syringe.

12. A method as recited in claim 1, wherein said adapter means, said first catheter cartridge means, and said second catheter cartridge means are sized for use with an infant patient.

13. A method for selectively providing a plurality of different types of respiratory therapies in combination with an endotracheal tube, said method comprising the steps of:

providing adapter means adapted for connection to an end of an endotracheal tube, said adapter means comprising a pair of connection ports, at least one of said ports being adapted for connection to a ventilator means;

providing a plurality of interchangeable catheter cartridge means for providing any one of several desired types of respiratory therapies and adapted to be releasably and interchangeably connected to one of said ports, said plurality of catheter cartridge means including:

first catheter cartridge means for aspirating fluids therethrough and adapted for connection to a source of vacuum; and second catheter cartridge means, selectively interchangeable with said first catheter cartridge, for delivering a fluid through an endotracheal tube;

connecting one of said plurality of catheter cartridge means with said adapter means to form a first connection assembly; and disconnecting said one of said plurality of catheter cartridge means from said adapter means and connecting another of said plurality of catheter cartridge means with said adapter means to form a second connection assembly.

14. A method as recited in claim 13, wherein said adapter means comprises a Y-adapter for connection to an end of an endotracheal tube, said Y-adapter including a distal fitting adapted for connection to an endotracheal tube, a first proximal fitting adapted for connection to a ventilator means, and a second proximal fitting, said first and second proximal fittings of said Y-adapter comprising said pair of connection ports of said adapter means.

15. A method as recited in claim 14, wherein said first catheter cartridge means comprises a first catheter cartridge including an aspirating catheter enclosed within a collapsible sheath, a first connector for selective, releasable fluid-tight connection to said second proximal fitting of said Y-adapter, an integral wash chamber formed in said first connector surrounding a portion of said aspirating catheter, a liquid introduction assembly that carries liquid directly from a liquid dispensing container into said integral wash chamber without passing through said Y-adapter, a second connector adapted for fluid-tight connection to a source of vacuum, and valve means in fluid communication with said aspirating catheter and operable to selectively place said aspirating catheter and an endotracheal tube in communication with a source of vacuum to effect aspiration of fluids therethrough.

16. A method as recited in claim 15, wherein said second catheter cartridge means comprises a second catheter cartridge including a fluid delivery catheter enclosed within a collapsible sheath, a first connector for selective, releasable fluid-tight connection to said second proximal fitting of said Y-adapter so as to be selectively interchangeable with said first catheter cartridge, and a second connector for said fluid-tight connection to a source of fluid to be delivered.

17. A method as recited in claim 13, further including the step of providing a third catheter cartridge means for providing an additional type of respiratory therapy and selectively connecting said third catheter cartridge means with said adaptor means.

18. A method for selectively providing a plurality of different types of respiratory therapies in combination with an endotracheal tube, said method comprising the steps of:

providing a Y-adapter for connection to an end of an endotracheal tube, said Y-adapter comprising a distal fitting adapted for connection to an endotracheal tube, a first proximal fitting adapted for connection to a ventilator means, and a second proximal fitting;

providing a plurality of interchangeable catheter cartridges, each of which provides a desired types of respiratory therapy, said plurality of catheter cartridges including:

a first catheter cartridge adapted for connection to a source of vacuum comprising an aspirating catheter enclosed within a collapsible sheath, a first connector for selective, releasable fluid-tight connection to said second proximal fitting of said adapter means, an integral wash chamber formed in said first connector surrounding a portion of said aspirating catheter, a liquid introduction assembly that carries liquid directly from a liquid dispensing container into said integral wash chamber without passing through said Y-adapter, a second connector adapted for fluid-tight connection to a source of vacuum, and valve means in fluid communication with said aspirating catheter and operable to selectively place said aspirating catheter and an endotracheal tube in communication with a source of vacuum to effect aspiration of fluids therethrough; and a second catheter cartridge for delivery of fluid through an endotracheal tube comprising a fluid delivery catheter enclosed within a collapsible sheath, a first connector for selective, releasable fluid-tight connection to said second proximal fitting of the Y-adapter so as to be selectively interchangeable with said first catheter cartridge, and a second connector for fluid-tight connection to a source of fluid to be delivered;

selectively connecting said first and second catheter cartridges with said Y-adapter in order to form one or more desired connection assemblies for providing said variety of respiratory therapies.

19. A method as recited in claim 18, further including the steps of connecting one of said catheter cartridges with said Y-adapter in order to provide a first connection assembly, disconnecting said catheter cartridges from said Y-adapter and then connecting another of said catheter cartridges with said Y-adapter in order to provide a second connection assembly.

20. A method as recited in claim 18, wherein said Y-adapter includes a third proximal fitting and wherein said first and second catheter cartridges are connected to said Y-adapter simultaneously to thereby provide said variety of respiratory therapies.

21. A method as recited in claim 18, further including the steps of providing a third catheter cartridge which provides an additional type of respiratory therapy and selectively connecting said third catheter cartridge with said Y-adapter.

22. An apparatus for selectively providing a plurality of different types of respiratory therapies in combination with an endotracheal tube, said apparatus comprising:

adapter means adapted for connection to an end of an endotracheal tube, said adapter means comprising a pair of connection ports, at least one of said ports being adapted for connection to a ventilator means; and a plurality of interchangeable catheter cartridge means for providing any one of several desired types of respiratory therapies and adapted to be releasibly and interchangeably connected to one of said ports, said plurality of catheter cartridge means comprising:

first catheter cartridge means for aspirating fluids therethrough, adapted for connection to a source of vacuum, and comprising an aspirating catheter enclosed within a collapsible sheath, first connector means for selective, releasable fluid-tight connection to one of said ports of said adapter means, an integral wash chamber formed in said first connector means, liquid introduction means for carrying liquid directly from a liquid dispensing container into said integral wash chamber without passing through said adapter means, second connector means adapted for fluid-tight connection to a source of vacuum, and valve means in fluid communication with said aspirating catheter and operable to selectively place said aspirating catheter and an endotracheal tube in communication with a source of vacuum to effect aspiration of fluids therethrough; and second catheter cartridge means for delivering a fluid through an endotracheal tube and comprising a fluid delivery catheter enclosed within a collapsible sheath, first connector means for selective, releasable fluid-tight connection to said one of said ports of said adapter means so as to be selectively interchangeable with said first catheter cartridge means, and second connector means for fluid-tight connection to a source of fluid to be delivered, wherein said apparatus in a first arrangement of parts for providing aspiration of fluids comprises said first catheter cartridge means releasably connected to said adapter means, and wherein said apparatus in a second arrangement of parts for delivering a fluid through an endotracheal tube comprises said second catheter cartridge means releasably connected to said adapter means.

23. An apparatus as recited in claim 22, further including a third catheter cartridge means for providing an additional type of respiratory therapy, wherein said apparatus in a third arrangement of parts for providing said additional type of respiratory therapy comprises said third catheter cartridge means releasably connected to said adaptor means.

24. An apparatus as recited in claim 22, wherein said apparatus in an alternative arrangement of parts for selectively providing said aspiration of fluids and said delivery of a fluid through an endotracheal tube comprises said first and second catheter cartridge means being connected to said adaptor means simultaneously.

25. An apparatus as recited in claim 22, wherein said adaptor means comprises a Y-adaptor including a distal fitting adapted for connection to an endotracheal tube, a first proximal fitting adapted for connection to a ventilator means, and a second proximal fitting, said first and second proximal fittings of said Y-adaptor comprising said pair of connection ports of said adaptor means.

26. An apparatus as recited in claim 25, wherein said Y-adaptor includes a third proximal fitting adapted for connection to one of said plurality of interchangeable catheter cartridge means.

27. An apparatus for selectively providing a plurality of different types of respiratory therapies in combination with an endotracheal tube, said apparatus comprising:

adapter means adapted for connection to an end of an endotracheal tube, said adapter means comprising a pair of connection ports, at least one of said ports being adapted for connection to a ventilator means; and a plurality of interchangeable catheter cartridge means for providing any one of several desired types of respiratory therapies and adapted to be releasibly and interchangeably connected to one of said ports, said plurality of catheter cartridge means comprising:

first catheter cartridge means for aspirating fluids therethrough and adapted for connection to a source of vacuum; and second catheter cartridge means, selectively interchangeable with said first catheter cartridge, for delivering a fluid through an endotracheal tube, wherein said apparatus in a first arrangement of parts for providing aspiration of fluids comprises said first catheter cartridge means releasably connected to said adapter means, and wherein said apparatus in a second arrangement of parts for delivering a fluid through an endotracheal tube comprises said second catheter cartridge means releasably connected to said adapter means.

* * * * *